(12) United States Patent
Ouyang

(10) Patent No.: US 11,832,797 B2
(45) Date of Patent: Dec. 5, 2023

(54) ENDOSCOPIC FLUORESCENCE IMAGING

(71) Applicant: MICRONVISION CORP, Bellevue, WA (US)

(72) Inventor: Xiaolong Ouyang, Bellevue, WA (US)

(73) Assignee: MicronVision Corp., Bellevue, WA (US)

( * ) Notice: Subject to any disclaimer, the term of this patent is extended or adjusted under 35 U.S.C. 154(b) by 1218 days.

(21) Appl. No.: 16/363,209

(22) Filed: Mar. 25, 2019

(65) Prior Publication Data

US 2019/0216325 A1 Jul. 18, 2019

Related U.S. Application Data

(63) Continuation-in-part of application No. PCT/US2017/053171, filed on Sep. 25, 2017.

(Continued)

(51) Int. Cl.
*A61B 1/04* (2006.01)
*A61B 1/06* (2006.01)
(Continued)

(52) U.S. Cl.
CPC .......... *A61B 1/043* (2013.01); *A61B 1/00009* (2013.01); *A61B 1/00052* (2013.01);
(Continued)

(58) Field of Classification Search
CPC ......... A61B 1/043; A61B 1/05; A61B 1/0676; A61B 1/00105; A61B 1/051; A61B 1/063;
(Continued)

(56) References Cited

U.S. PATENT DOCUMENTS 4,854,302 A 8/1989 Allred, III
4,979,497 A 12/1990 Matsura
(Continued)

FOREIGN PATENT DOCUMENTS

CN 102858275 1/2013
EP 1690512 8/2006
(Continued)

OTHER PUBLICATIONS

Jul. 1, 2019 International Preliminary Report on Patentability in connection with PCT/US2017/053171 and dated Mar. 8, 2018 Article 34 Amendment and Demand for International Preliminary Examination Under Chapter II of PCT.
(Continued)

*Primary Examiner* — Ryan N Henderson
(74) *Attorney, Agent, or Firm* — Wissing Miller LLP

(57) ABSTRACT

Systems and methods are configured for combined fluorescence imaging and white light imaging of tissue such as during surgical endoscopic procedures. A chip-on-tip type endoscope can be equipped with both white light and blue light LEDs. A single camera or dual cameras are configured with backside illuminated CMOS image sensor(s) to receive and process the white light and fluorescence images. The light sources, image sensors and image processing circuitry are configured to synchronously emit light and record pixels for visible white light and fluorescence frames alternately. Global or quasi-global shuttering can be used on the image sensor(s). A modified color filter array and other filters can be provided to enhance fluorescence imaging capabilities. Insufflating gas clears debris from the camera field of view and aids in moving the cannula distally through a body passageway.

10 Claims, 17 Drawing Sheets

Related U.S. Application Data

(60) Provisional application No. 62/647,817, filed on Mar. 25, 2018, provisional application No. 62/654,295, filed on Apr. 6, 2018, provisional application No. 62/671,445, filed on May 15, 2018, provisional application No. 62/816,366, filed on Mar. 11, 2019, provisional application No. 62/399,429, filed on Sep. 25, 2016, provisional application No. 62/399,436, filed on Sep. 25, 2016, provisional application No. 62/399,712, filed on Sep. 26, 2016, provisional application No. 62/405,915, filed on Oct. 8, 2016, provisional application No. 62/423,213, filed on Nov. 17, 2016, provisional application No. 62/424,381, filed on Nov. 18, 2016, provisional application No. 62/428,018, filed on Nov. 30, 2016, provisional application No. 62/429,368, filed on Dec. 2, 2016, provisional application No. 62/485,454, filed on Apr. 14, 2017, provisional application No. 62/485,641, filed on Apr. 14, 2017, provisional application No. 62/502,670, filed on May 6, 2017, provisional application No. 62/550,188, filed on Aug. 25, 2017, provisional application No. 62/550,560, filed on Aug. 25, 2017, provisional application No. 62/550,581, filed on Aug. 26, 2017, provisional application No. 62/558,818, filed on Sep. 14, 2017.

(51) Int. Cl.
| | |
|---|---|
| *A61B 1/045* | (2006.01) |
| *A61B 1/00* | (2006.01) |
| *A61B 1/05* | (2006.01) |
| *A61B 5/00* | (2006.01) |
| *A61B 1/307* | (2006.01) |
| *A61M 13/00* | (2006.01) |
| *A61B 1/12* | (2006.01) |
| *G02B 21/16* | (2006.01) |
| *A61B 1/015* | (2006.01) |

(52) U.S. Cl.
CPC ...... *A61B 1/00096* (2013.01); *A61B 1/00186* (2013.01); *A61B 1/015* (2013.01); *A61B 1/045* (2013.01); *A61B 1/05* (2013.01); *A61B 1/051* (2013.01); *A61B 1/0607* (2013.01); *A61B 1/0638* (2013.01); *A61B 1/0655* (2022.02); *A61B 1/126* (2013.01); *A61B 1/307* (2013.01); *A61B 5/0071* (2013.01); *A61M 13/003* (2013.01); *G02B 21/16* (2013.01); *A61B 2562/0233* (2013.01); *A61M 2210/1085* (2013.01)

(58) Field of Classification Search
CPC ... A61B 1/0638; A61B 1/0646; A61B 1/0653; A61B 1/0655; A61B 1/307; A61B 1/0607; A61B 1/045; A61B 1/015; A61B 1/00186; A61B 1/00096; A61B 1/0009; A61B 5/0071
See application file for complete search history.

(56) References Cited

U.S. PATENT DOCUMENTS

| | | |
|---|---|---|
| 5,010,876 A | 4/1991 | Henley |
| 5,188,093 A | 2/1993 | Lafferty |
| 5,281,214 A | 1/1994 | Wilkins |
| 5,323,767 A | 6/1994 | Lafferty |
| 5,329,936 A | 7/1994 | Lafferty |
| 5,390,117 A | 2/1995 | Graf et al. |
| 5,486,155 A | 1/1996 | Muller |
| 5,549,547 A | 8/1996 | Cohen |
| 5,569,163 A | 10/1996 | Francis |
| 5,666,561 A | 9/1997 | Stephenson |
| 5,667,472 A | 9/1997 | Finn |
| 5,667,476 A | 9/1997 | Frassica et al. |
| 5,785,644 A | 7/1998 | Grabover |
| 5,860,953 A | 1/1999 | Snoke |
| 5,873,814 A | 2/1999 | Adair |
| 5,928,137 A | 7/1999 | Green |
| 5,935,141 A | 8/1999 | Weldon |
| 5,957,947 A | 9/1999 | Wattiez |
| 6,007,531 A | 12/1999 | Snoke |
| 6,007,546 A | 12/1999 | Snow |
| 6,017,322 A | 1/2000 | Snoke |
| 6,033,378 A | 3/2000 | Lundquist |
| 6,059,719 A | 5/2000 | Yamamato et al. |
| 6,095,970 A | 8/2000 | Hidaka |
| 6,174,307 B1 | 1/2001 | Daniel |
| 6,210,416 B1 | 4/2001 | Chu |
| 6,211,904 B1 | 4/2001 | Adair |
| 6,221,007 B1 | 4/2001 | Green |
| 6,221,070 B1 | 4/2001 | Tu et al. |
| 6,261,226 B1 | 7/2001 | McKenna |
| 6,280,386 B1 | 8/2001 | Alfano et al. |
| 6,331,174 B1 | 12/2001 | Reinhard |
| 6,387,043 B1 | 5/2002 | Yoon |
| 6,398,743 B1 | 6/2002 | Halseth |
| 6,507,699 B2 | 1/2003 | Lemoine |
| 6,518,823 B1 | 2/2003 | Kawai |
| 6,793,882 B1 | 9/2004 | Verschuur |
| 6,917,380 B1 | 7/2005 | Tay |
| 7,256,446 B2 | 8/2007 | Hu |
| 7,428,378 B1 | 9/2008 | Warpakowski |
| 7,507,205 B2 | 3/2009 | Borovsky |
| 7,591,799 B2 | 9/2009 | Selkee |
| 7,606,609 B2 | 10/2009 | Muranushi |
| 7,780,650 B2 | 8/2010 | Frassica |
| 7,798,995 B2 | 9/2010 | Yue |
| 7,931,616 B2 | 4/2011 | Selkee |
| 7,946,981 B1 | 5/2011 | Cubb |
| 8,052,609 B2 | 11/2011 | Harhen |
| 8,057,464 B2 | 11/2011 | Chen |
| 8,187,171 B2 | 5/2012 | Irion |
| 8,197,398 B2 | 6/2012 | Scholly |
| 8,235,975 B2 | 8/2012 | Chen |
| 8,361,775 B2 | 1/2013 | Flower |
| 8,460,182 B2 | 6/2013 | Ouyang |
| 8,523,808 B2 | 9/2013 | Selkee |
| 8,696,552 B2 | 4/2014 | Whitman |
| 8,803,960 B2 | 8/2014 | Sonnenschein |
| 8,834,357 B2 | 9/2014 | Oskin |
| 8,845,522 B2 | 9/2014 | McIntyre |
| 8,952,312 B2 | 2/2015 | Blanqart |
| 8,998,844 B2 | 4/2015 | Reed |
| 9,649,014 B2 | 5/2017 | Ouyang |
| 9,736,342 B2 | 8/2017 | Mueckl |
| 9,895,048 B2 | 2/2018 | Ouyang |
| 10,278,563 B2 | 5/2019 | Ouyang |
| 10,292,571 B2 | 5/2019 | Ouyang |
| 2001/0007051 A1 | 7/2001 | Nakashima |
| 2001/0049509 A1 | 12/2001 | Sekine |
| 2003/0016284 A1 | 1/2003 | Squilla |
| 2003/0023142 A1 | 1/2003 | Grabover |
| 2003/0078476 A1 | 4/2003 | Hill |
| 2003/0078502 A1 | 4/2003 | Miyaki et al. |
| 2003/0151680 A1 | 8/2003 | McDermott |
| 2003/0199735 A1 | 10/2003 | Dickopp |
| 2004/0054254 A1 | 3/2004 | Miyake |
| 2004/0054259 A1 | 3/2004 | Hasegawa |
| 2004/0138558 A1 | 7/2004 | Dunki-Jacobs |
| 2004/0162572 A1 | 8/2004 | Sauer |
| 2005/0010178 A1 | 1/2005 | Katz |
| 2005/0264687 A1 | 1/2005 | Murayama |
| 2005/0049459 A1 | 3/2005 | Hern |
| 2005/0085695 A1 | 4/2005 | Sherner |
| 2005/0154262 A1 | 7/2005 | Banik |
| 2005/0159646 A1 | 7/2005 | Nordstrom |
| 2005/0177027 A1 | 8/2005 | Hirata |
| 2005/0277874 A1 | 12/2005 | Selkee |
| 2005/0277875 A1 | 12/2005 | Selkee |

(56) References Cited

U.S. PATENT DOCUMENTS

| | | |
|---|---|---|
| 2006/0052710 A1 | 3/2006 | Miura |
| 2006/0063976 A1 | 3/2006 | Aizenfeld |
| 2006/0114986 A1 | 6/2006 | Knapp |
| 2006/0152601 A1 | 7/2006 | Parekh |
| 2006/0167340 A1 | 7/2006 | Peas |
| 2006/0171693 A1 | 8/2006 | Todd |
| 2006/0173245 A1 | 8/2006 | Todd |
| 2006/0259124 A1 | 11/2006 | Matsuoka |
| 2006/0287576 A1 | 12/2006 | Tsuji |
| 2007/0060789 A1 | 3/2007 | Uchimura |
| 2007/0081920 A1 | 4/2007 | Murphy |
| 2007/0117437 A1 | 5/2007 | Boehnlein |
| 2007/0129604 A1 | 6/2007 | Hatcher |
| 2007/0162095 A1 | 7/2007 | Kimmel |
| 2007/0167678 A1 | 7/2007 | Moskowitz |
| 2007/0167868 A1 | 7/2007 | Sauer |
| 2007/0173693 A1 | 7/2007 | Refael |
| 2007/0188604 A1 | 8/2007 | Miyamoto |
| 2007/0197875 A1 | 8/2007 | Osaka |
| 2007/0210162 A1 | 9/2007 | Keen |
| 2007/0225556 A1 | 9/2007 | Ortiz |
| 2007/0238927 A1 | 10/2007 | Ueno |
| 2008/0004642 A1 | 1/2008 | Birk |
| 2008/0071144 A1 | 3/2008 | Kimmel |
| 2008/0097550 A1 | 4/2008 | Dicks |
| 2008/0108869 A1 | 5/2008 | Sanders |
| 2008/0195125 A1 | 8/2008 | Orbay |
| 2008/0195128 A1 | 8/2008 | Orbay |
| 2008/0225410 A1 | 9/2008 | Ning |
| 2008/0234547 A1 | 9/2008 | Irion et al. |
| 2008/0255416 A1 | 10/2008 | Gilboa |
| 2008/0262306 A1 | 10/2008 | Kawai |
| 2008/0300456 A1 | 12/2008 | Irion |
| 2009/0027489 A1 | 1/2009 | Takemura |
| 2009/0065565 A1 | 3/2009 | Lemoine |
| 2009/0076321 A1 | 3/2009 | Suyama |
| 2009/0076328 A1 | 3/2009 | Root |
| 2009/0080214 A1 | 3/2009 | Watanabe |
| 2009/0105538 A1 | 4/2009 | Van Dam |
| 2009/0118580 A1 | 5/2009 | Sun |
| 2009/0118641 A1 | 5/2009 | Van Dam |
| 2009/0149713 A1 | 7/2009 | Niida |
| 2009/0225159 A1 | 9/2009 | Schneider |
| 2009/0227897 A1 | 9/2009 | Wendt |
| 2009/0286412 A1 | 11/2009 | Ikeda |
| 2009/0287663 A1 | 11/2009 | Takeuchi |
| 2010/0069834 A1 | 3/2010 | Schultz |
| 2010/0094216 A1 | 4/2010 | Yue |
| 2010/0095969 A1 | 4/2010 | Schwartz |
| 2010/0101569 A1 | 4/2010 | Kim |
| 2010/0121142 A1 | 5/2010 | Ouyang |
| 2010/0157039 A1 | 6/2010 | Sugai |
| 2010/0160914 A1 | 6/2010 | Bastian |
| 2010/0168827 A1 | 7/2010 | Schultz |
| 2010/0191051 A1 | 7/2010 | Miyake |
| 2010/0191053 A1 | 7/2010 | Garcia |
| 2010/0234736 A1 | 9/2010 | Corl |
| 2010/0026201 A1 | 10/2010 | Frangioni |
| 2011/0009694 A1 | 1/2011 | Schultz |
| 2011/0034769 A1 | 2/2011 | Adair |
| 2011/0037876 A1 | 2/2011 | Talbert |
| 2011/0054446 A1 | 3/2011 | Schultz |
| 2011/0092775 A1 | 4/2011 | Deshmukh |
| 2011/0105839 A1 | 5/2011 | Hoffman |
| 2011/0112622 A1 | 5/2011 | Phan |
| 2011/0130627 A1 | 6/2011 | McGrail |
| 2011/0211115 A1 | 9/2011 | Tsai |
| 2011/0213206 A1 | 9/2011 | Boutillette |
| 2011/0245602 A1 | 10/2011 | Brannon |
| 2011/0288482 A1 | 11/2011 | Farrell |
| 2012/0016191 A1 | 1/2012 | Ito |
| 2012/0040305 A1 | 2/2012 | Karazivan |
| 2012/0053515 A1 | 3/2012 | Crank |
| 2012/0100729 A1 | 4/2012 | Edidin |
| 2012/0165627 A1* | 6/2012 | Yamamoto ............ A61B 1/063 600/317 |
| 2012/0165916 A1 | 6/2012 | Jordan |
| 2012/0178991 A1 | 7/2012 | Clark |
| 2012/0226103 A1 | 9/2012 | Gunday |
| 2012/0236138 A1 | 9/2012 | Liu |
| 2012/0245242 A1 | 9/2012 | Peiffer |
| 2012/0245418 A1 | 9/2012 | Boulais |
| 2012/0253116 A1 | 10/2012 | Sniffin |
| 2012/0259203 A1 | 10/2012 | Devereux |
| 2012/0286020 A1 | 11/2012 | Smith |
| 2012/0289858 A1* | 11/2012 | Ouyang ................ A61B 1/045 600/562 |
| 2013/0035553 A1 | 2/2013 | Kongstorum |
| 2013/0046142 A1 | 2/2013 | Remijan |
| 2013/0057667 A1 | 5/2013 | McGrath |
| 2013/0150672 A1 | 6/2013 | Fujitani |
| 2013/0172676 A1 | 7/2013 | Levy |
| 2013/0225921 A1 | 8/2013 | Liu |
| 2013/0253402 A1 | 9/2013 | Badawi |
| 2013/0289559 A1 | 10/2013 | Reid |
| 2013/0324973 A1 | 12/2013 | Reed |
| 2013/0345514 A1 | 12/2013 | Manion |
| 2014/0022649 A1 | 1/2014 | Echhardt |
| 2014/0107416 A1 | 4/2014 | Bimkrant |
| 2014/0111634 A1 | 4/2014 | Mueckl |
| 2014/0154399 A1 | 6/2014 | Weikart |
| 2014/0180007 A1 | 6/2014 | Edidin |
| 2014/0213848 A1 | 7/2014 | Moskowitz |
| 2014/0228635 A1 | 8/2014 | Tuliakov |
| 2014/0275763 A1 | 9/2014 | King |
| 2014/0296866 A1 | 10/2014 | Salman |
| 2014/0323991 A1 | 10/2014 | Tang |
| 2015/0005575 A1 | 1/2015 | Kobayashi |
| 2015/0011830 A1 | 1/2015 | Hunter |
| 2015/0018622 A1 | 1/2015 | Tesar |
| 2015/0018710 A1 | 1/2015 | Furlong |
| 2015/0088001 A1 | 3/2015 | Lindvold et al. |
| 2015/0150441 A1 | 6/2015 | Ouyang |
| 2015/0164313 A1* | 6/2015 | Ouyang ............ A61B 1/00105 600/103 |
| 2015/0196197 A1* | 7/2015 | Kienzle ............ A61B 17/3478 600/478 |
| 2015/0238251 A1 | 8/2015 | Shikhman |
| 2015/0297311 A1 | 10/2015 | Tesar |
| 2016/0007833 A1* | 1/2016 | Huang .................. A61B 1/128 600/109 |
| 2016/0073853 A1 | 3/2016 | Venkatesan et al. |
| 2016/0077008 A1 | 3/2016 | Takasu et al. |
| 2016/0174819 A1* | 6/2016 | Ouyang ............ A61B 1/00098 600/105 |
| 2016/0334694 A1 | 11/2016 | Liu |
| 2016/0367119 A1* | 12/2016 | Ouyang ............ A61B 1/0676 |
| 2017/0086651 A1 | 3/2017 | Sato |
| 2017/0188793 A1 | 7/2017 | Ouyang |
| 2017/0188795 A1* | 7/2017 | Ouyang ................ A61B 1/018 |
| 2017/0215699 A1 | 8/2017 | Ouyang |
| 2017/0295347 A1 | 10/2017 | Schneider |
| 2017/0310858 A1 | 10/2017 | Mueckl |
| 2018/0132700 A1 | 5/2018 | Ouyang |
| 2018/0184892 A1 | 7/2018 | Truckai |
| 2018/0235441 A1 | 8/2018 | Huang |
| 2018/0256009 A1 | 9/2018 | Ouyang |
| 2019/0000308 A1* | 1/2019 | Duckett, III ....... A61B 1/00105 |
| 2019/0029497 A1 | 1/2019 | Mirza |
| 2019/0110686 A1* | 4/2019 | Kato ................... A61B 5/0071 |
| 2019/0142262 A1 | 5/2019 | Inglis |
| 2019/0216325 A1 | 7/2019 | Ouyang |
| 2019/0223691 A1 | 7/2019 | Takatsuji |
| 2019/0246873 A1 | 8/2019 | Lu |
| 2019/0246884 A1 | 8/2019 | Lu et al. |
| 2019/0282073 A1 | 9/2019 | Truckai |
| 2019/0320879 A1 | 10/2019 | Langell |
| 2019/0374095 A1 | 12/2019 | Lord |
| 2020/0204776 A1 | 6/2020 | Themelis |
| 2020/0214739 A1 | 7/2020 | Shi |
| 2020/0275827 A1 | 9/2020 | Weise |

(56) References Cited

U.S. PATENT DOCUMENTS

| | | |
|---|---|---|
| 2021/0228806 A1 | 7/2021 | Streeter |
| 2021/0401277 A1 | 12/2021 | Ouyang |

FOREIGN PATENT DOCUMENTS

| | | |
|---|---|---|
| EP | 2560589 | 4/2010 |
| EP | 3384879 | 4/2011 |
| EP | 2749258 | 7/2014 |
| EP | 3078354 | 10/2016 |
| JP | 2009148420 | 7/2009 |
| WO | 2011133792 | 10/2011 |
| WO | 2012060932 | 5/2012 |
| WO | 2014031192 | 2/2014 |
| WO | 2014065901 | 5/2015 |
| WO | 2016032729 | 3/2016 |
| WO | 2016040131 | 3/2016 |
| WO | 2016137838 | 9/2016 |
| WO | WO 2016/137838 A1 | 9/2016 |
| WO | 2018136950 | 7/2018 |
| WO | 2019237003 | 12/2019 |

OTHER PUBLICATIONS

International Search Report and Written Opinion of PCT/US2016/18670, dated Jul. 12, 2016.
International Search Report and Written Opinion of PCT/US2018/014880, dated Jun. 6, 2018.
International Search Report and Written Opinion of PCT/US2018/065396, dated Feb. 24, 2017.
International Search Report and Written Opinion of PCT/US2021/050095 dated Dec. 17, 2021.
International Search Report and Written Opinion of PCT/US2019/036060 dated Aug. 27, 2019.
International Search Report and Written Opinion of PCT/US2017/053171 dated Dec. 5, 2017.
International Preliminary Report on Patentability of PCT/US2017/053171 completed on Jul. 1, 2019.
Extended European Search Report of European Patent Application No. EP19816177 completed Feb. 2, 2022.
International Search Report and Written Opinion of the International Searching Authority dated Dec. 5, 2017 in connection with PCT/US17/53171.
Mar. 6, 2018 Letter Accompanying Amendment under Article 34 and Demand For International Preliminary Examination under Chapter II of the PCT in connection with PCT/US17/53171.

\* cited by examiner

| Time axis | 610 T-White | 612 T-Blue | 614 T-White | 616 T-Blue |
|---|---|---|---|---|
| Light source | white light | blue light | white light | blue light |
| Sensor readout | Global shutter readout of the entire array (RGBR) | Global shutter readout of R array only | Global shutter readout of the entire array (RGBR) | Global shutter readout of R array only |
| Image processing | white light frames | Red color band frames | white light frames | Red color band frames |

*FIG. 6A*

| Time axis | 610<br>◄---- T-White ----► | 612<br>◄---- T-Blue ----► | 614<br>◄---- T-White ----► | 616<br>◄---- T-Blue ----► |
|---|---|---|---|---|
| Light source | white light | blue light | white light | blue light |
| Sensor readout | Global shutter readout of the entire array (RGBR) | Global shutter readout of R array only | Global shutter readout of the entire array (RGBR) | Global shutter readout of R array only |
| Image processing | white light frames | Red color band frames | white light frames | Red color band frames |

FIG. 6B

ENDOSCOPIC FLUORESCENCE IMAGING

REFERENCE TO RELATED APPLICATIONS

This patent application claims the benefit of and incorporates by reference each of the following provisional applications:
U.S. Prov. Ser. No. 62/647,817 filed Mar. 25, 2018;
U.S. Prov. Ser. No. 62/654,295 filed Apr. 6, 2018;
U.S. Prov. Ser. No. 62/671,445 filed May 15, 2018; and
U.S. Prov. Ser. No. 62/816,366 filed Mar. 11, 2019.

This patent application is a continuation (with added subject matter) of International Patent Application No. PCT/US17/53171 filed Sep. 25, 2017, which claims the benefit of and incorporates by reference each of the following provisional applications:
U.S. Prov. Ser. No. 62/399,429 filed Sep. 25, 2016;
U.S. Prov. Ser. No. 62/399,436 filed Sep. 25, 2016;
U.S. Prov. Ser. No. 62/399,712 filed Sep. 26, 2016;
U.S. Prov. Ser. No. 62/405,915 filed Oct. 8, 2016;
U.S. Prov. Ser. No. 62/423,213 filed Nov. 17, 2016;
U.S. Prov. Ser. No. 62/424,381 filed Nov. 18, 2016;
U.S. Prov. Ser. No. 62/428,018 filed Nov. 30, 2016;
U.S. Prov. Ser. No. 62/429,368 filed Dec. 2, 2016;
U.S. Prov. Ser. No. 62/485,454 filed Apr. 14, 2017;
U.S. Prov. Ser. No. 62/485,641 filed Apr. 14, 2017;
U.S. Prov. Ser. No. 62/502,670 filed May 6, 2017;
U.S. Prov. Ser. No. 62/550,188 filed Aug. 25, 2017;
U.S. Prov. Ser. No. 62/550,560 filed Aug. 25, 2017;
U.S. Prov. Ser. No. 62/550,581 filed Aug. 26, 2017; and
U.S. Prov. Ser. No. 62/558,818 filed Sep. 14, 2017.

All of the above-referenced non-provisional, provisional and international patent applications are hereby incorporated in this application by reference and are collectively referenced herein as "the commonly assigned incorporated applications."

FIELD

This patent specification generally relates mainly to a medical device for use in tissue examinations. More particularly, some embodiments relate to devices and methods for fluorescence imaging in medical applications such as visually detecting tissues such as tumors, nerves, and vessels during surgical procedures.

BACKGROUND

Endoscopic fluorescence imaging systems can be used to detect tissue such as tumors and vessels during surgical procedures. Infrared dyes can be used as tagging dyes for marking tissue. Some endoscopic fluorescence imaging systems are capable of acquiring high resolution images in the normal white light visible spectrum, while simultaneously acquiring and overlaying the infrared signal on top of normal visible spectrum images in order to provide a contrast to a surgeon while operating. Some systems are designed to detect unbound intravascular indocyanine green (ICG), an FDA approved NIR (near infrared) fluorescent dye. ICG is typically intravenously administered in high doses, and imaging is performed 30-60 minutes after injection. The intravascular fluorescent load achieved with this approach is high, and approved clinical imaging devices have adequate sensitivity for these applications. Examples of such systems include a fluorescent module incorporated into operating microscopes (OPMI Pentero Infrared 800, Carl Zeiss), as well at the SPY® and Pinpoint® systems (Novadaq), and the FluoBeam® 800 (Fluoptics) hand-held unit. While these systems may have adequate sensitivity for intravascular imaging, they may lack practical use in other applications such as targeted tumor-specific NIR fluorescence due to low sensitivity. In simultaneous visible and NIR capture imaging systems, one camera captures the image in the visible spectrum and second camera captures the fluorescent image. This is achieved by splitting the incident light from the field into two channels using a beam-splitter. One beam transmits the NIR fluorescent light to one of the cameras, while the other beam of visible light passes through the beam splitter into the second camera. See, e.g., U.S. Pat. No. 8,961,403 B2.

U.S. Pat. No. 9,407,838 discusses a system suitable for lab analysis or high-end surgical applications that can simultaneously record a visible light image and an infrared light image from fluorescent dye. The discussed system simultaneously uses a laser for emitting excitation light for an infrared or near-infrared fluorophore and a visible light source. The discussed system also includes a notch beam splitter, a notch filter, a synchronization module, an image sensor for simultaneously detecting both visible light and infrared light, an image processing unit for image subtraction after capture, an image displaying unit, and light-conducting channels.

The subject matter described or claimed in this patent specification is not limited to embodiments that solve any specific disadvantages or that operate only in environments such as those described above. Rather, the above background is only provided to illustrate one exemplary technology area where some embodiments described herein may be practiced.

SUMMARY

According to some embodiments, a single-use, disposable cannula for multi-band imaging of a patient's bladder has a distal tip and comprises: a light source configured to illuminate said bladder with white light during first time intervals and with non-white excitation light causing fluorescence from selected tissue during second time intervals time-interleaved with said first time intervals; and an imaging structure configured to receive both said fluorescence and reflections of said white light from the bladder; wherein said imaging structure comprises a single, multi-pixel, backside-illuminated, two-dimensional light sensor array and a readout circuit electrically and physically integrated therewith into a circuit stack; wherein said imaging structure is configured to respond to said reflections to generate a white light image of the bladder and to said fluorescence to produce a fluorescence image of the bladder; and wherein the white light and fluorescence images are both spatially and temporally registered with each other.

According to some embodiments: the imaging structure includes respective color filters for pixels of said sensor array, causing some of said pixels to receive said fluorescent and others to receive said reflections; the cannula includes a global shutter configured to essentially concurrently read the pixels of said sensor array; the cannula includes a quasi-global shutter configured to essentially concurrently read only one or more selected subsets of the pixels of said sensor array; an agent introduced in the bladder preferentially induces cancerous tissue to emit said fluorescence; said second time intervals are longer than said first time intervals; the excitation light has a wavelength in the range 350-450 nanometers; the fluorescence has a wavelength in the range of 580-720 nanometers; and/or the sensor array receives only the reflected white light during said first time intervals and only the fluorescence during said second time intervals.

According to some embodiments, the cannula is combined with a handle to which the cannula is releasably secured through electrical and mechanical couplers tool-free by hand and detached tool-free by hand, and said handle may further comprise a physically integral video screen coupled with said sensor array to receive and display said white light and fluorescent images.

According to some embodiments: the cannula further includes a shield keeping said excitation light from said sensor array; said white light and excitation light illuminate the same field of illumination in the bladder; and/or said imaging structure comprises a spatially repeating pattern of red, green, and blue pixel filters through which light from the bladder passes to reach said sensor array.

According to some embodiments, the cannula is enclosed in a sterile packaging and is a single-use, disposable unit.

According to some embodiments: the cannula further includes a source of a second, different excitation light causing fluorescence from the bladder during third time intervals interleaved in time with said first and second time intervals, and said imaging structure is configured to receive fluorescence from the bladder during the second and third time intervals and produce spatially registered white light and two fluorescence images.

According to some embodiments, the cannula comprises a distal portion at which said imaging structure is situated and a proximal portion, and further comprises an inlet port that is at the proximal portion of the cannula and is configured to receive insufflating gas, an outlet port that is at the distal portion of the cannula, and a gas conduit between said proximal and distal ports, wherein said distal port is configured to direct gas delivered thereto through said conduit in a flow over said imaging structure that clears a field of view of the imaging portion.

According to some embodiments, said distal port is configured to extend said gas flow in a distal direction to aid in moving said distal portion of the cannula through a patient's body passageway by helping dilate the passageway; said distal portion of the cannula comprises an outer shell that surrounds said imaging structure and said gas conduit comprises spacing between the outer shell and the imaging structure; said spacing radially surrounds the entire imaging structure; said spacing is only at one or more arcs around the imaging structure; said outer shell extends distally further than said imaging structure and comprises a lip bent radially inwardly to direct said gas glow over the imaging structure; and/or said lip extends over only a part of the circumference of said outer shell.

According to some embodiments, the cannula further includes a manually adjustable gas flow control having an output for receiving gas from a source and an output connected for gas flow to said input port; and/or further includes a pressure gauge showing gas pressure fed to said input port. The source of the insufflating gas can be a conventional threaded $CO_2$ cartridge that contains less than 10 grams of carbon dioxide, thus helping keep an entire set of a cannula, handle and gas source easily hand-held and portable.

According to some embodiments, an endoscope comprises a single-use, disposable cannula for multi-band imaging of a patient's bladder and a reusable handle that is releasably connected to said cannula through electrical and mechanical connectors, wherein (a) said cannula has a distal tip that comprises: a light source configured to illuminate said bladder with white light during first time intervals and with non-white excitation light causing fluorescence from selected tissue during second time intervals time-interleaved with said first time intervals; and an imaging structure configured to receive both said fluorescence and reflections of said white light from the bladder and in response to produce a white light image of the bladder and a fluorescence image of the bladder that are both spatially and temporally registered with each other; an input port for insufflating gas, a distal outlet port for said gas at a distal portion of the cannula, and a gas conduit connecting the input and distal ports; wherein said distal port is configured to direct a flow of said gas over a field of view of said imaging structure to clear debris from said field of view; and (b) said handle comprises an integral display screen configured to display images taken with said imaging structure.

According to some embodiments, in said endoscope: said distal port comprises an outer shell that at least partly surrounds said imaging structure and directs said gas over a distal face of the imaging structure; said conduit comprises space between the outer shell and the imaging structure; and/or said distal port is further configured to direct gas flow distally of said distal tip of the cannula to aid in moving said distal tip through a patient's body passageway.

According to some embodiments, the endoscope further includes a gas flow controller having an input for gas and an output feeding gas to said distal port of the cannula; and/or said imaging structure comprises an imaging sensor and a processor in a stacked arrangement.

According to some embodiments, a method of imaging a patient's inner bladder wall comprises: Illuminating said inner bladder wall with white light during first time intervals and with non-white excitation light causing fluorescence from selected tissue during second time intervals time-interleaved with said first time intervals; receiving both said fluorescence and reflections of said white light from the bladder wall at an imaging structure that is at a tip of a cannula, and in response producing a white light image of the bladder wall and a fluorescence image of the bladder wall that are both spatially and temporally registered with each other; and supplying insufflating gas at a distal port of said cannula to create a gas flow over a field of view of the imaging structure that aids in clearing debris from said field of view.

According to some embodiments, said supplying step further comprises creating a gas flow that extends distally of said distal tip of the cannula to aid in moving said distal tip through a patient's body passageway.

As used herein, the grammatical conjunctions "and", "or" and "and/or" are all intended to indicate that one or more of the cases, object or subjects they connect may occur or be present. In this way, as used herein the term "or" in all cases indicates an "inclusive or" meaning rather than an "exclusive or" meaning.

As used herein the terms "surgical" or "surgery" refer to any physical intervention on a patient's tissues and does not necessarily involve cutting a patient's tissues or closure of a previously sustained wound.

BRIEF DESCRIPTION OF THE DRAWINGS

To further clarify the above and other advantages and features of the subject matter of this patent specification, specific examples of embodiments thereof are illustrated in the appended drawings. It should be appreciated that these drawings depict only illustrative embodiments and are therefore not to be considered limiting of the scope of this patent specification or the appended claims. The subject matter hereof will be described and explained with additional specificity and detail through the use of the accompanying drawings in which:

FIGS. 6A and 6B are charts illustrating some aspects of the timing of illuminating light sources and sensor exposures for combined fluorescence and white light endoscopy imaging, according to some embodiments;

DETAILED DESCRIPTION

A detailed description of examples of preferred embodiments is provided below. While several embodiments are described, the new subject matter described in this patent specification is not limited to any one embodiment or combination of embodiments described herein, but instead encompasses numerous alternatives, modifications, and equivalents. In addition, while numerous specific details are set forth in the following description in order to provide a thorough understanding, some embodiments can be practiced without some or all of these details. Moreover, for the purpose of clarity, certain technical material that is known in the related art has not been described in detail in order to avoid unnecessarily obscuring the new subject matter described herein. It should be clear that individual features of one or several of the specific embodiments described herein can be used in combination with features of other described embodiments or with other features. Further, like reference numbers and designations in the various drawings indicate like elements.

Figure 1A:
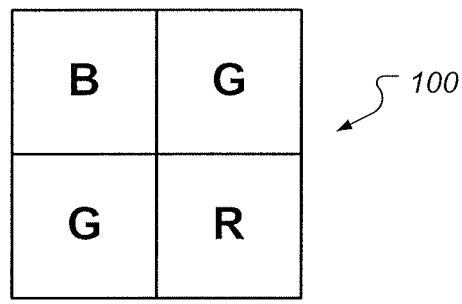
FIGS. 1A and 1B are diagrams illustrating aspects of a conventional CMOS image sensor.
Figure 1B:
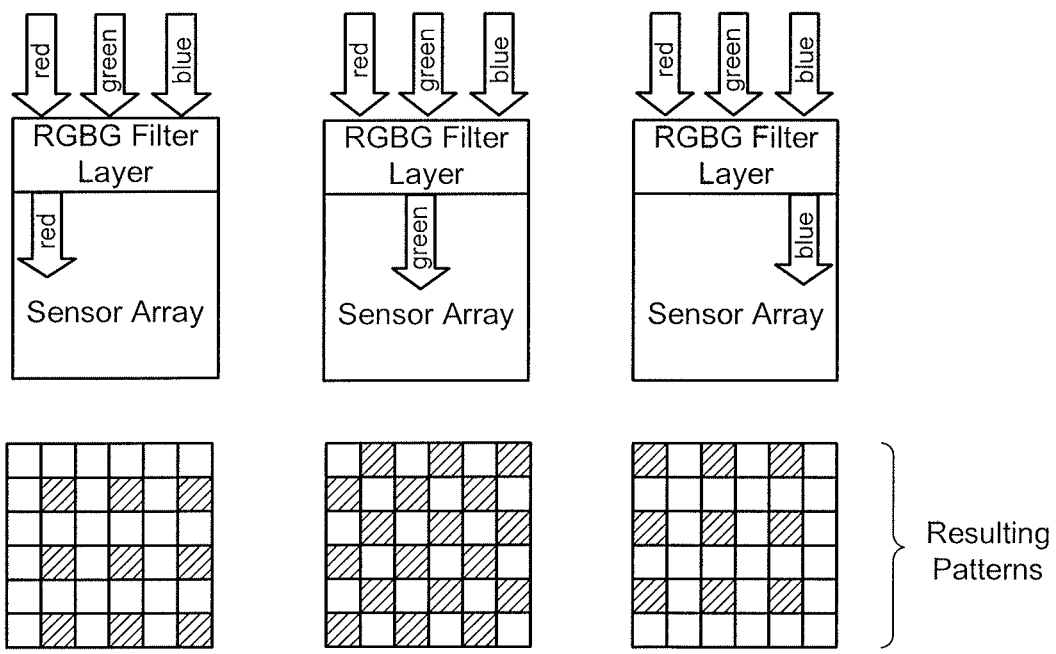

FIGS. 1A and 1B are diagrams illustrating aspects of a conventional CMOS image sensor. A color image is captured using a color filter array (CFA), where the sensor pixels are masked with red (R), green (G) and blue (B) filters. A 2×2 portion 100 of a common conventional CFA known as a Bayer filter is shown in FIG. 1A. As shown in FIG. 1B, each color band image is captured by a separate sub-group of pixels of the sensor pixel array. A full-color image, with intensities of all three primary colors represented by each pixel, is then synthesized by merging the separate sub pixel group using a de-mosaicing algorithm. As shown in FIG. 1A, the standard Bayer filter CFA has 2G 1R 1B or "RGBG". With this arrangement, more pixels are allocated to G, because the human eye is most sensitive to green (around 550 nm) and most natural images have high green content.

In medical imaging, fluorescence techniques allow visualization of features that are invisible or are not easily visible under conventional white light. According to some embodiments, a video endoscope system is provided for fluorescence endoscopy. A protocol is also described to combine the fluorescence endoscopy with white light endoscopy. According to some embodiments, dual color band or multi-color band imaging systems are described herein that provide improved visualization of tissue using combined fluorescence and white light endoscopy.

Figure 2:
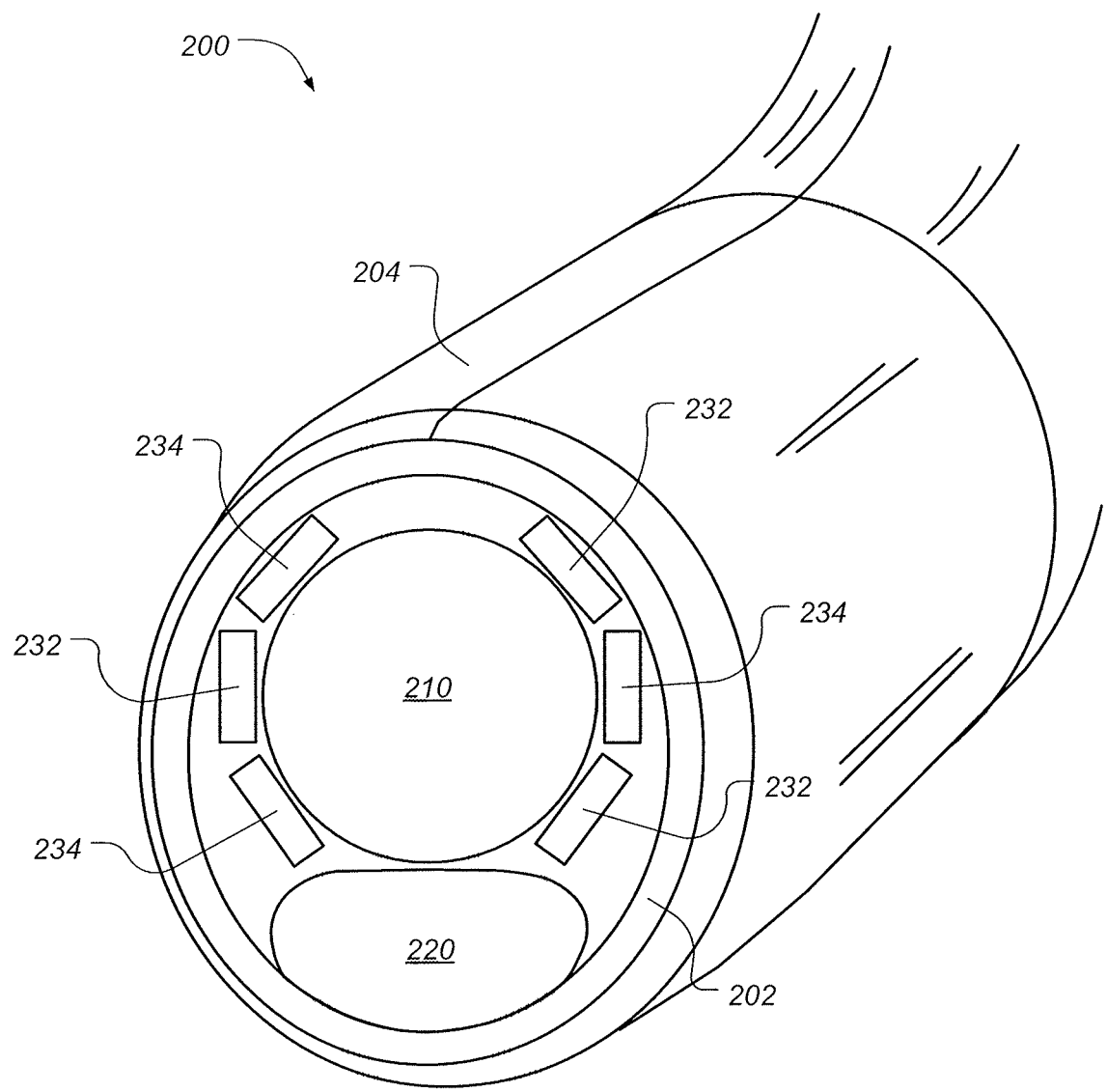
FIG. 2 is a diagram showing aspects of a distal tip assembly of multi-color band endoscope, according to some embodiments.

FIG. 2 is a diagram showing aspects of a distal tip assembly of a multi-band or multi-color band endoscope, according to some embodiments. According to some embodiments, the endoscope 200 is disposable, or partially disposable after single-use. Endoscopes with disposable cannulas that include a distal tip with a camera are discussed in U.S. Patent Appl. Publ. No. 2016/0367119, and U.S. Pat. No. 9,895,048 which are incorporated herein by reference. Other examples of endoscopes with disposable cannulas are discussed in U.S. Pat. No. 9,622,646, also incorporated herein by reference. The distal tip assembly 204 includes a lens/sensor barrel 210 that includes a camera module having a color sensor with a color filter array, and electronics and circuitry as will be described in further detail, infra. Surrounding the lens/sensor barrel 210 are blue LEDs 232 and white LEDs 234. The blue LEDs 232 are configured to emit excitation light suitable for fluorescence endoscopy. In some examples, the blue LEDs 232 are configured to emit light at about 410 nm (violet-blue). The white LEDs 234 are configured to emit white light suitable for visible white light endoscopy. Below the lens/sensor barrel 210 is a port 220 that is configured to provide fluid (flowing either into or out of the patient) and/or provide an opening through which a tool or other device can pass (e.g. a needle). According to some embodiments, the port 220 is greater than 1.0 mm in its smallest dimension. According to some embodiments, the LEDs 232 and 234 are approximately 0.75 mm×0.25 mm. The outer wall 202, according to some embodiments, is at least 0.25 mm thickness and is appropriately rounded to avoid any sharp edges. According to some embodiments, the lens/sensor barrel 210 and the LEDs 232 and 234 can be recessed so that a dome shaped cover can be placed so as to further ensure smoothness of the distal tip. According to some embodiments, the outer diameter of the tip assembly is 12 Fr to 15 Fr (4 mm to 5 mm), and preferably is no more than 6 mm as the outside diameter of outer wall 202. Note that although FIG. 2 shows a total of six LEDs (three white and three blue), in general, other numbers of LEDs may be provided according to factors such as desired lighting quality, endoscope size, and LED characteristics such as size and brightness. In some embodiments four or fewer LEDs can be provided and in some embodiments 10 or more LEDs can be provided. Furthermore, the number of white and blue LEDs does not have to be equal, but also will depend on various factors. Other light sources can be substituted, such as optic fibers that deliver light generated elsewhere.

Figure 3A:
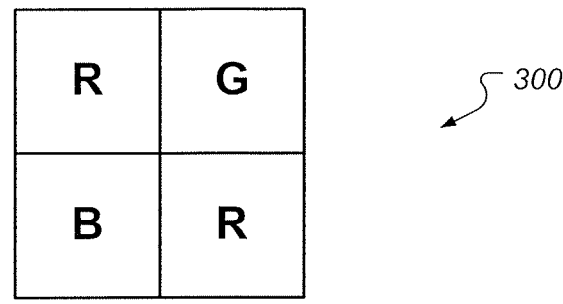
FIGS. 3A and 3B are diagrams illustrating aspects of a CMOS image sensor system having improved visualization of tissue using combined fluorescence and white light endoscopy, according to some embodiments.
Figure 3B:
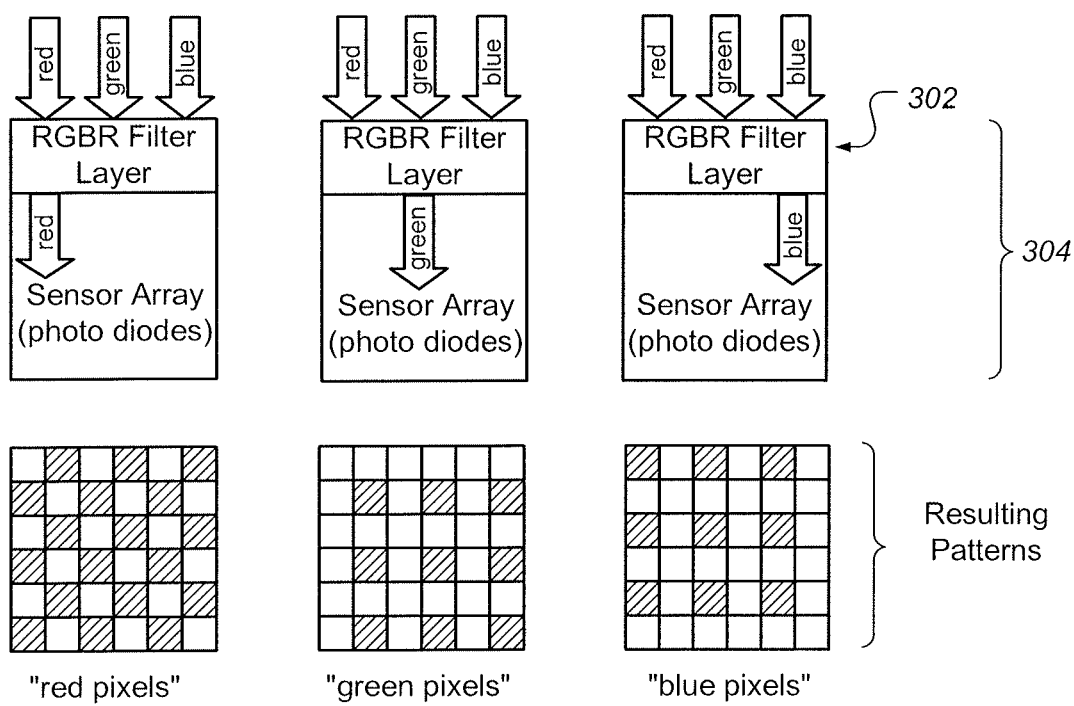

FIGS. 3A and 3B are diagrams illustrating aspects of a CMOS image sensor system having improved visualization of tissue using combined fluorescence and white light endoscopy, according to some embodiments. In FIG. 3A a 2×2 portion 300 is shown of an RGBR color filter array. A color filter array having the shown pattern will have red resolution roughly 2 times greater than that of blue or green. As can be seen in FIG. 3B, when the RGBR color filter layer 302 is used, the sensor array 304 has enhanced sensitivity to fluorescence light coming from the tissues of interest during an endoscopic procedure. According to some embodiments, the sensor array 304 and RGBR color filter 302 are used in the camera module of endoscope 200 shown in FIG. 2.

According to some embodiments, endoscope 200 can be used for differential imaging of a patient's bladder to determine the presence and characteristics of cancerous tissue. In this example of use, the color filter array 302 is configured to enhance sensitivity to pink-red light (about 610 nm wavelength) by selecting a pattern that preferentially passes pink-red to sensor array 304. The image provided by pink-red light preferentially shows cancerous tissue emitting fluorescent light in that color, typically due to the appropriate dye or other agent introduced in the patient at an appropriate time before imaging. Such dyes or other agents are known in the art of fluorescence medical imaging.

According to some embodiments, endoscope 200 can be used for differential imaging of a patient's nerves to assist in surgery where it may be desirable to identify nerve tissue so as to avoid damaging such tissue or to perform procedures on such tissue. In this example of use, the color filter array 302 is configured to enhance sensitivity to dark green light (about 510 nm wavelength) by selecting a pattern that preferentially passes dark green to sensor array 304. A filter such as in FIG. 3A but with a pattern RGBG can be used for the purpose. The image provided by dark green light preferentially shows nerve tissue emitting fluorescent light in that color, typically due to the appropriate dye or other agent introduced in the patient at an appropriate time before imaging. Such dyes or other agents are known in the art of fluorescence medical imaging.

According to some embodiments, light sources 234 can provide light other than white light, sources 232 can provide different color(s) excitation light, and color filter 302 can preferentially pass light in different color(s) to sensor 304, to thereby preferentially image selected tissue with light of a first wavelength range incident on sensor 304 and other selected tissue with light of a second wavelength range, different from the first range, incident on sensor 304.

FIGS. 3A and 3B illustrate one example of a filter array 302 but other examples of filter arrays that enhance sensing different colors at sensor 304 are possible. While using a white light image and a color image such as pink-red, or dark green are given as examples, other combinations of images may be useful for imaging patients' tissue, and fluorescent images in two or more colors may be useful. Typically, sensor array 304 is read in alternating or at least interspersed time intervals, for example alternating white image and color image time intervals. The resulting white and color images typically are shown composited, in geometric registration, so that the position of selected tissue such as cancerous tissue or nerve tissue can be visualized relative to surrounding anatomy, but separate white and color images can be displayed instead or in addition.

Figure 4A:
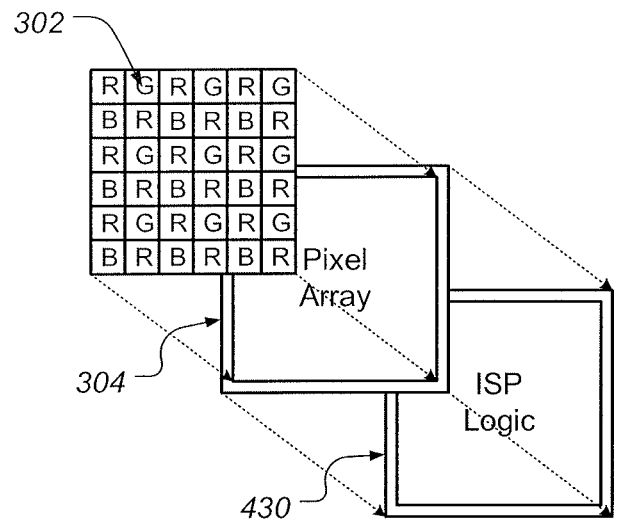
FIGS. 4A and 4B are schematic diagrams illustrating aspects of a stacked CMOS image sensor system having improved visualization of tissue using combined fluorescence and white light endoscopy, according to some embodiments.
Figure 4B:
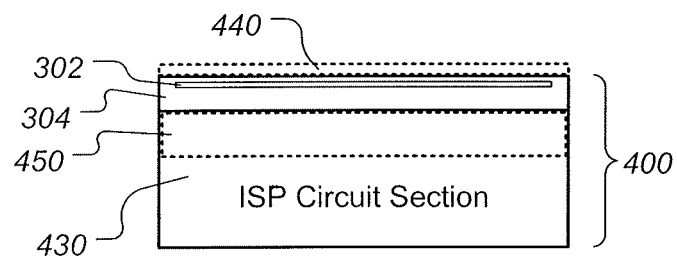

FIGS. 4A and 4B are schematic diagrams illustrating aspects of a stacked CMOS image sensor system having improved visualization of tissue using combined fluorescence and white light endoscopy, according to some embodiments. FIG. 4A depicts RGBR color filter 302 formed within an upper portion of sensor array 304, which includes backside-illuminated (BSI) CMOS photo diodes. The sensor array 304 is bonded directly to a logic circuit chip 430 that contains an image signal processor (ISP). FIG. 4B is a side view of the BIS CMOS image sensor (CIS) stack 400 containing the RGBR color filter array 302 and logic circuit chip 430. Using a 3D stacked image sensor 400 consisting of a BSI image sensor die face-to-face stacked on a logic die containing an image signal processor (ISP) has a number of advantages for combined fluorescence and white light endoscopy applications, one of which is the ability to use global shuttering and/or quasi-global shuttering. The stacked image sensor and ISP arrangement shown in FIGS. 4A and 4B allows for readout of the entire area of the pixel array simultaneously. The image can be captured simultaneously using all pixels. According to some embodiments, the image sensor/ISP architecture includes a memory structure and additional MOS transistors to provide additional functionality and increased read-out speed. Another benefit of using a stacked image sensor in endoscopy applications is that the fast read-out times allow for higher quality moving image capabilities which is desirable for imaging during surgical procedures. Furthermore, the use of stacked arrangement such as shown in FIGS. 4A and 4B allows for a more compact sensor chip since the circuit section of the chip does not take up additional sensor chip surface area. Having a compact sensor chip is beneficial in chip-on-tip endoscopy applications since it is desirable to reduce the frontal area occupied by the camera module.

According to some embodiments, stack 400 can be a stacked back-illuminated structure similar to a stacked BSI CMOS device from Sony in the family of devices offered under the trade designation Exmor RS sensors. Preferably, stack 400 is an integrated, single-chip device comprising individual photo-diodes, each under a respective color filter through which light from tissue passes before impinging on the photo-diode, metal wiring under the photodiodes, and image processing circuitry under the metal wiring to read the electrical output of the photo-diodes and convert it to image information to be sent for further processing and/or display. One example of such stack is designated Sony Exmor RS sensor stack IMX 398, which comprises a 12 MP sensor (4608×3456) and has a 6.4 mm diagonal dimension. The stack comprises a sensor layer and a logic layer that is behind the sensor layer and contains readout circuits to read out the electrical signals that the sensor pixels provide in response to light. For use in endoscope 200, the diagonal dimension of sensor stack 400 preferably is no more than 3 mm, more preferably no more than 2 mm, and even more preferably no more than 1.5 mm. This can be accomplished by reducing the number of pixels in the sensor, for example to a number sufficient to provide lower spatial resolution such as 400×400, or by shrinking the dimensions of sensor elements such as photo-diodes, or both.

According to some embodiments, the stacked arrangement can include one or more additional filters 440 to further enhance combined fluorescence and white light endoscopy imaging. For example, filters 440 often include an infrared (IR) filter configured to suppress IR sensitivity, or a different color filter configured to suppress sensitivity to a different color as required for a specific tissue or specific use of endoscope 200. Filters 440 can also include a band pass filter that is configured to allow passage of wavelengths around 600 nm, or some other wavelength(s) that coincide with fluorescent light coming from the tissues of interest. Further examples of possible filters are shown and described with respect to FIG. 5, infra. According to some embodiments, the stacked arrangement can include further layers, such as a DRAM layer 450 (shown in FIG. 4B) that can be configured to store signals read at high speed temporarily, enabling even shorter read-out times. A stack 400 with a built-in DRAM layer can be similar in structure to, but preferably smaller than, a device offered by Sony under the designation Exmor RS IMX 400. In this case, the stack comprises a sensor layer, a DRAM layer, and a logic (readout) layer, stacked in the direction of the light that illuminates the sensor layer. A built-in DRAM layer for temporary storage of images need not be used when the read-out circuitry in stack 400 is sufficiently fast to send the image information from sensor array 304 essentially in real time to processing circuitry elsewhere, such as in handle 940 (FIG. 9) or in display 950 (FIG. 9), where the output of stack 400 can be converted into images for display and/or storage. According to some embodiments, the stacked CMOS image sensor system(s) shown in FIGS. 4A and 4B are used in the camera module of endoscope 200 shown in FIG. 2.

Figure 5:
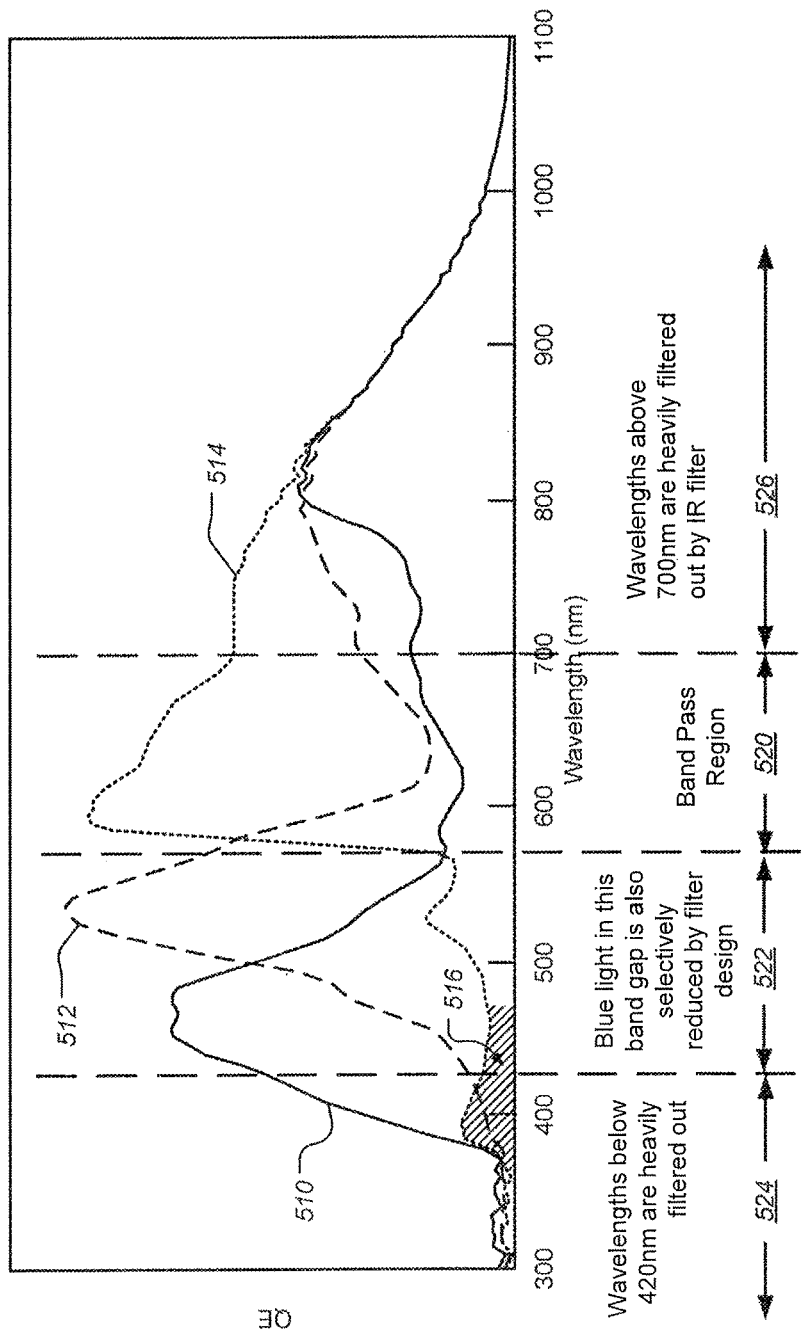
FIG. 5. is a diagram illustrating aspects of a filter configured to enhancing capture of fluorescence light during combined fluorescence and white light endoscopy imaging, according to some embodiments.

FIG. 5. is a diagram illustrating aspects of a filter configured to enhance capture of fluorescence light during combined fluorescence and white light endoscopy imaging, according to some embodiments. Shown in the main plot are curves 510, 512 and 514 which are pixel response curves for respective colors in an example of a CMOS sensor array. One or more filters, such as filter(s) 440 shown in FIG. 4B, can be configured to allow passage of light in region 520. According to some embodiments, wavelengths below about 420 nm (region 524) and above 700 nm (region 526) are heavily filtered out. According to some embodiments, the filter(s) can be further configured selectively to reduce light having wavelengths in region 522. Note that in practice the precise filtering characteristics and wavelengths blocked and/or passed will depend on the materials and structures used for filtering.

The reduction in region 522 has been found to be useful in reducing the amount of blue light "background" or "noise" that is recorded by the "red pixels" (the pixels associated with "R" in the color filter array). As can be seen in FIG. 5, a typical CMOS pixel response curve for red pixels, curve 514, has some non-zero response in the blue region (region 522). In particular, the cross-hatched area 516 represents that the red pixels will pick up light in the region near the fluorescence excitation source light (e.g. from 350 nm to 450 nm). Since the excitation source light in fluorescence endoscopy can be several times brighter than the resultant fluorescence light, the excitation light can show up as background or noise in the red pixel image. It has been found that by selectively suppressing the blue light in the region 522, and especially near the wavelengths of the source light, the background noise can be greatly reduced in the red pixel image. The amount of reduction in 522 can be tailored to the particular characteristics of the sensor and image processing used, as well as the particular surgical application(s) the endoscope is directed to. The design of filter 440 should also account for the properties of the color filter array 302 (shown in FIGS. 3B, 4A and 4B). For example, in many cases the color filter array 302 will heavily filter out wavelengths below 420 nm. In such cases the filter 440 can be configured to heavily reduce infrared light greater than 700 nm, and selectively reduce blue light in the region 522 to reduce blue light background from the red pixels. According to some embodiments, some or all of filtering aspects of filter 440 described herein can be integrated into the design of the color filter array 302. For example, for suppressing the blue light background recorded by the red pixels in the region 522, the described blue light suppression can be partially or fully accomplished by color filter array 302. Specifically, the red filter portions of filter 302 can be configured to suppress more light in region 522 than red filters in typical CFA designs (e.g. curve portion 516). According to some embodiments, filter 440 can be a liquid crystal tunable filter (LCTF) that can be selectively switched between being clear or nearly clear so it is essentially transparent and being in a state in which it blocks or significantly attenuates some wavelengths, as is described in further detail with respect to FIG. 7, infra.

FIGS. 6A and 6B are charts illustrating some aspects of the timing of illuminating light sources and sensor exposures for combined fluorescence and white light endoscopy imaging, according to some embodiments. Four time intervals 610, 612, 614 and 616 are shown wherein white light sources (e.g. White LEDs 234 in FIG. 2) and blue light sources (e.g. Blue LEDs 232 in FIG. 2) are alternately activated. During the T-White intervals 610 and 614 the white light sources are energized while the global shutter allows passage of white light and are read out of the entire sensor array (e.g. of sensor 304 in FIGS. 4A and 4B). Image processing is pre-formed for the white light frames. Using all of the pixels the white light frames are processed, for example, using ISP circuitry 430 and possibly other processors. During the T-Blue intervals 612 and 616 the blue light sources are energized while the global shutter is set to filter out or significantly attenuate selected wavelengths such as in the blue region and are read out of the R pixels from the sensor array (e.g. of sensor 304 in FIGS. 4A and 4B). Image processing is performed for the red color band frames. Using all of the "R" pixels, the red light frames are processed, for example, using ISP circuitry 430 and possibly other processors. Thus, illumination light (white or blue) is synchronized with the appropriate global shuttering and image processing. The alternately captured white light video and sub-band video (R pixels) present different information of the object being imaged. The white light band image presents a normal view of the object, while the sub-band light image presents additional information about the object. According to some embodiments, the two video types are overlaid by the system processor. In medical applications, displaying the composite video allows clinicians to locate a tissue of interest (e.g. a diseased tissue) because the sub-band image precisely "highlights" the tissue of interest within an ordinary white light background image. This type of overlying or compositing is particularly useful in endoscopic surgical procedures.

According to some embodiments, the time periods can alternate between white and a color but in other embodiments the periods can be interspersed in a different sequence, for example in the sequence T-white, T-blue, T-blue, T-white, T-blue, T-white, etc. In addition, two or more colors can be included in the same sequence of time intervals, for example to form a sequence T-white, T-blue, T-red, T-white, etc.

According to some embodiments, the image processing can be configured differently for the white and red color band frames to further enhance visualization. For example, during the T-Blue intervals (612 and 616) the relative weights of the three-color channels are manipulated to enhance the visibility of the fluorescent tissue. The red channels can be boosted while the blue channels can be suppressed, by adjusting their relative gains. This will enhance the fluorescent tissue while reducing blue reflectance from the excitation light source (the blue LEDs).

According to some embodiments, in addition to alternating the white and blue light illumination, the duration of the blue (and/or other color(s)) and white light intervals can be manipulated to provide enhanced imaging for certain applications. For example, in some cases the fluorescence image may be too weak compared to the white image. In such cases the T-White and T-Blue interval timing can be configured such that the T-Blue intervals 612 and 616 are longer than the T-White intervals 610 and 614. In some examples, the T-Blue intervals can be 2 or more times longer than the T-White intervals so that the fluorescence image in enhanced over the white image.

According to some embodiments, quasi-global shuttering can be used in some cases instead of full global shuttering. Especially in case of a lower cost, smaller sized pixel array, quasi global shuttering can be used wherein the pixels in an entire column (or row) are read out in series, but all of the columns (or rows) are read out simultaneously. In this case each column (or row) has a dedicated analog to digital converter (ADC). For example, if the array size is 400×400 pixels (and the pixel size is about 2.2 um×2.2 um to 3.0 um×3.0 um) with a pixel read-out time of 5 u secs, each column (or row) can be read-out in about 2 ms, which leaves plenty of time for exposure (30+ ms for exposure at 30 frames per second). Note that in such quasi-global shuttering embodiments, the sensor readout in the T-Blue intervals (612 and 616) will include all of the pixel data, and the non-red pixel data can simply be ignored when forming the red color band frames.

Figure 7:
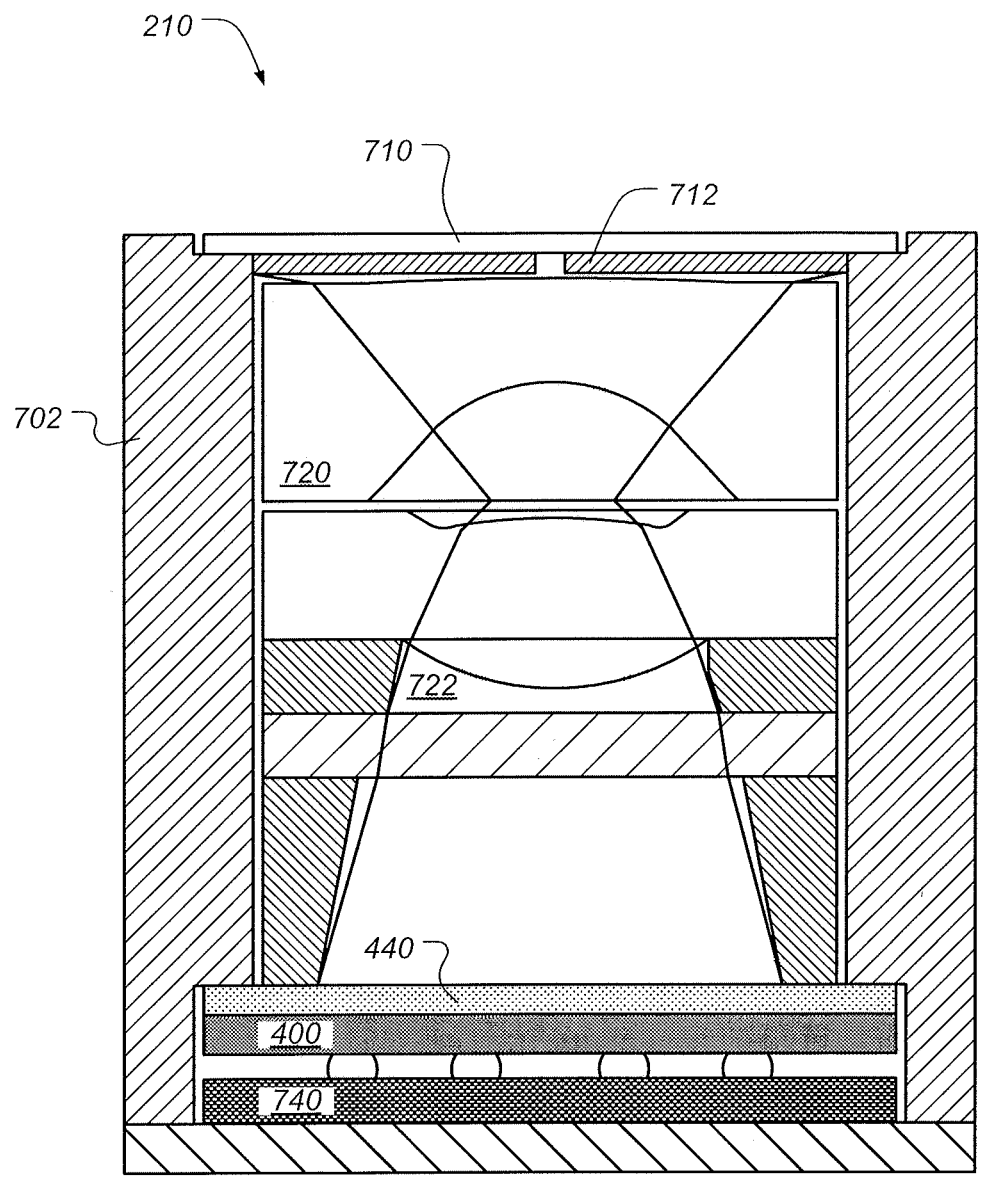
FIG. 7 is a cross sectional diagram illustrating aspects of a camera module configured for fluorescence endoscopy, according to some embodiments.

FIG. 7 is a cross sectional diagram illustrating aspects of a camera module configured for fluorescence endoscopy, according to some embodiments. The cross section shows a camera module and includes the lens/sensor barrel 210 which is also visible in FIG. 2. The outer body of the module is housed by camera module holder 702. The lens cover 710 overlies iris 712. One or more lens components are housed within holder 702, such as lens components 720 and 722 in this example shown. A BIS CMOS image sensor (CIS) stack 400 is shown bonded to circuit board 740 in this example. According to some embodiments, the CMOS sensor stack 400 includes an RGBR color filter array such as filter layer 302 shown in FIGS. 3B, 4A and 4B. One or more filters 440 are shown overlaid on the sensor stack 400. According to some embodiments, the filter(s) 440 can include a tunable filter, such as liquid crystal tunable filter (LCTF), that uses electronically controlled liquid crystal (LC) elements to transmit a selectable wavelength of light and exclude or suppress others. The LCTF filter can be dynamically controlled by a system processor to be in one of two states that are synchronized with the timing of illumination, global shutter (or quasi-global) capture mode, and image processing, as shown in FIGS. 6A and 6B. During the T-White intervals, (610 and 614 in FIGS. 6A and 6B) the LCTF filter is set to a "clear" state to allow passage of all colors of the spectrum. During the T-Blue intervals (612 and 616 in FIGS. 6A and 6B) the LCTF filter is set to a "blue" state which blocks most of all of the blue light from entering the sensor 304. In this way, the captured fluorescence light signal can be significantly enhanced by greatly reducing the undesirable background blue light or other spurious fluorescence or phosphorescence light while the white light images are unaffected.

Figure 8:
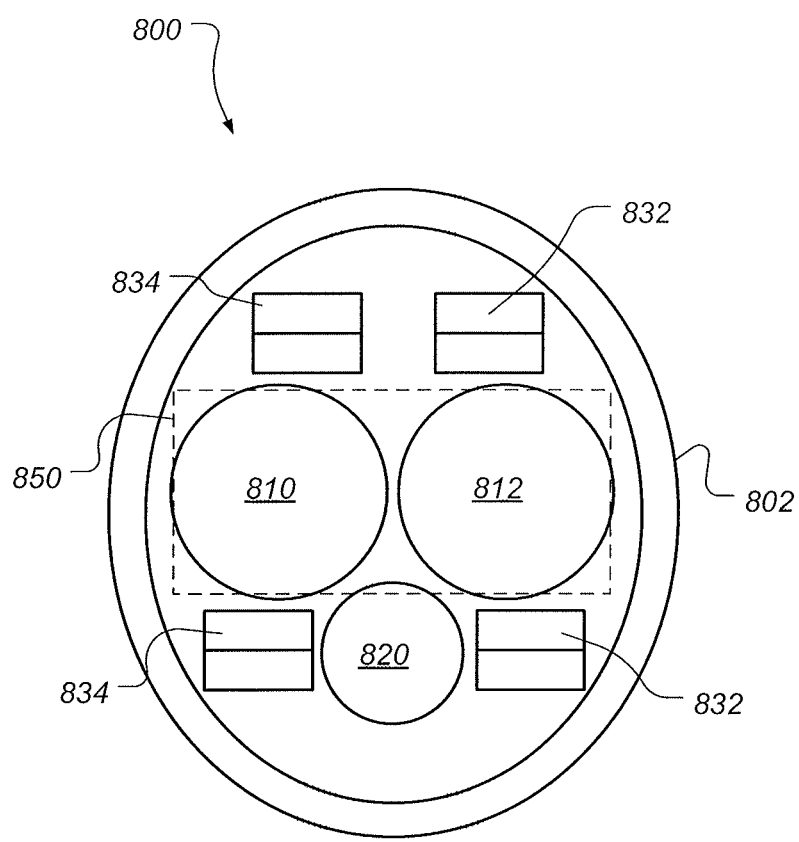
FIG. 8 is a diagram showing aspects of a distal tip assembly having dual camera modules, according to some other embodiments.

FIG. 8 is a diagram showing aspects of a distal tip assembly having dual camera modules, according to some other embodiments. According to some embodiments, the endoscope portion 800 is disposable, or partially disposable after single-use, as in the case of endoscope portion 204 shown in FIG. 2. The distal tip assembly in this case includes two camera modules: a white camera module 810 and a blue camera module 812. The white camera module 810 includes a CMOS sensor having an ordinary color filter array (as shown in FIGS. 1A and 1B), while the blue camera module 812 is specially configured to image the fluorescent light. According to some embodiments, the blue camera module 812 has no color filter array, but rather has a pass band filter with a narrow pass band corresponding to the fluorescent light (e.g. 600 nm or 610 nm). According to some embodiments, a single stacked CIS chip structure 850 can be used for both camera modules 810 and 812. In such cases, the stacked CIS structure is configured to selectively read out the portion of the sensor structure belonging to the white camera module and blue camera module during the appropriate intervals. Surrounding the camera modules 810 and 812 are a number of blue LEDs 832 and white LEDs 834. The blue LEDs 832 are configured to emit excitation light suitable for fluorescence endoscopy. In some examples, the blue LEDs 832 are configured to emit light at about 410 nm. The white LEDs 834 are configured to emit white light suitable for visible white light endoscopy. Also visible is a port 820 that is configured to provide fluid (flowing either into or out of the patient), and/or provide an opening through which a tool or other device can pass (e.g. a needle). According to some embodiments, the port 820 has an inner diameter of 1.0 mm, and the outer diameter of the entire tip is less than 6 mm on its largest dimension.

According to some embodiments, the blue camera module 812 is optimized to maximize sensitivity to the fluorescence light, while minimizing interference from other light sources. Since in this example the CMOS sensor does not have a CFA which would cause loss of incoming light, a filter can be used to block the undesirable blue light from entering the image sensor. According to some embodiments, a combined filter or separate filter can also be used to block undesired spurious fluorescence not originated from the targeted tissue. A combined filter or separate filter can also be used to block undesired spurious phosphorescence light from entering the blue camera. According to some embodiments, a band pass filter can be used that blocks all the wavelengths below about 580 nm and in the infrared band. One or more filters can be placed either in front of the camera lens (e.g. between the outermost element and the iris, or outside the iris. Alternatively, or in addition, the filter(s) can form part of the sensor lens stack (such as shown with filter(s) 440 in FIG. 7).

Figure 9:
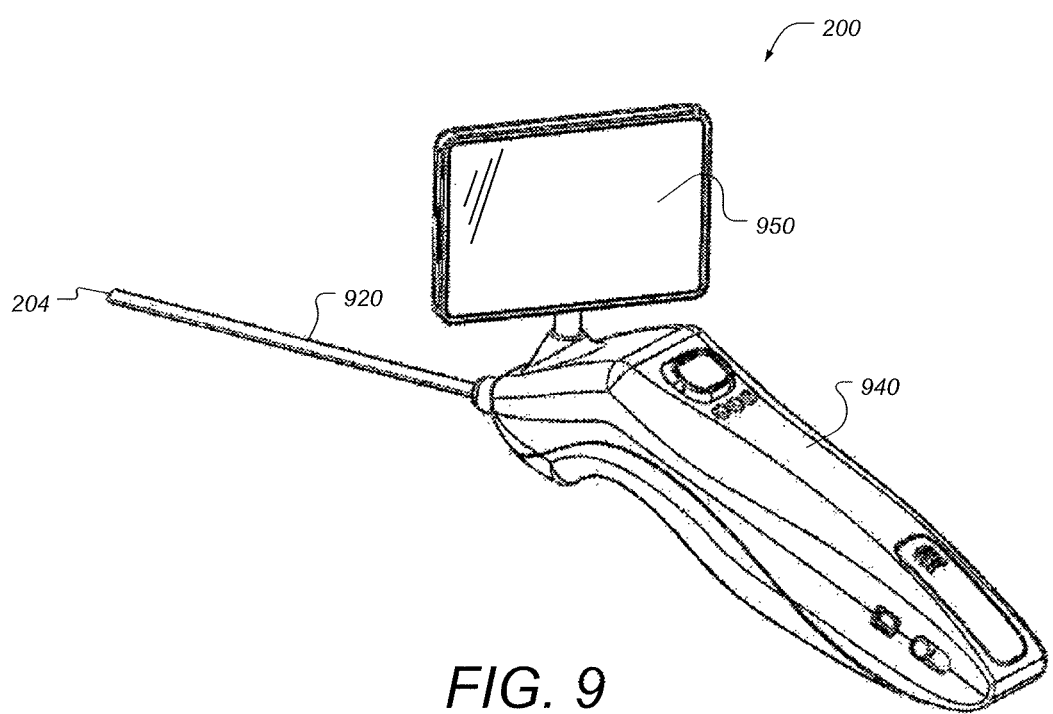
FIG. 9 is a perspective view of a handheld multi-color band endoscope, according to some embodiments.

FIG. 9 is a perspective view of a handheld multi-color band endoscope, according to some embodiments. The endoscope 200 includes an elongated cannula 920 with a distal tip 204 for inserting into a hollow organ or cavity of the body. Note that further details of tip 204 are shown in FIG. 2, supra. According to some embodiments, tip 204 includes a camera module and white and blue LEDs, as is shown in more detail in FIG. 2, and/or other colors. According to some embodiments, tip 204 can include dual camera modules such as shown in FIG. 8, supra. According to some embodiments, the distal end of the cannula 920 can also be slightly bent.

The endoscope 200 includes a handle portion 940 that is sized and shaped for easy grasping by the endoscope operator (e.g. doctor or other medical professional). According to some embodiments, the cannula 920 includes a fluid channel which is fluidly connected to a proximal fluid port (not shown) and port 220 (shown in FIG. 2). According to some embodiments, the channel within the cannula 920 can also be used as working channel via a proximal opening (not shown). According to some embodiments, a re-usable portions of endoscope 200 is removably mounted to enable some portions of endoscope 200 to be re-used while other portions intended to be disposed of after single-use. For example, endoscope 200 can be configured with a connector between the handle portion 940 so it can be detached from cannula 920, as discussed for the endoscope shown in FIGS. 1 and 2 of said pending U.S. application Ser. No. 14/913,867. In this case the cannula 920, including the distal tip 204 can be disposed of after a single-use while the handle portion 940 (including electronics and a re-chargeable battery) and display module 950 can be re-used many times. Other configurations are possible. For example, in some embodiments the display module 950 includes much or all of the electronics and a re-chargeable battery, and the display module is configured to be removable from the handle portion 940. In this case the handle portion 940 and cannula 920 can be configured and intended to be disposed of after a single use while the display module 950 can be re-used many times. Display 950 can be removably mounted on the upper side of handle portion 940 as shown. By making some portions of the device 200 all single-use, stringent decontamination and disinfection procedures, as well as the risk of cross-contamination and hospital acquired diseases, can be significantly lessened or avoided. Endoscope tip 204 alternatively can be used as a part of a non-disposable endoscope cannula, if made such that it can be suitably decontaminated between patients.

A distal portion of cannula 920 can be bent so tip 204 can point to the tissue to be imaged, as in the case of the tip portion of the cannula in FIGS. 1 and 2 of said application Ser. No. 14/913,867. When the tip portion is bent in this manner, the professional using endoscope 200 can rotate it around the long axis of cannula 920 such that tip 204 points to the desired tissue.

If desirable to change the orientation of tip 204 relative to the long axis of cannula 920, endoscope 200 can be provided with a facility to deflect tip 204 relative to cannula 920 before and/or during a patient examination. For example, a distal portion of cannula 920 can be made of a material that can be bent and retains its shape after being bent, so that a desired angle between tip 204 and the long axis of cannula 920 can be set before introducing cannula 920 into a patient. If desirable to change the angle while cannula 920 is in a patient, endoscope 200 can be provided with a tip deflecting mechanism, for example of the type discussed in U.S. Pat. No. 9,549,666 B2, which is hereby incorporated by reference. Deflection of tip 204 relative to the long axis of cannula 920 can be arranged so it can be in a single plane, e.g., left-right deflection using two cables to pull tip 204 to the left or to the right (or up-down), or it can be to any angle, using more cables or an arrangement similar to that in said U.S. Pat. No. 9,549,666 B2.

Endoscope portions such as 200 and 800 can be used in endoscopes having other configurations, for example in endoscopes that have straight cannulas, have different handles, and different image displays, and in endoscopes in which the cannula is re-usable rather than being a single-use, disposable cannula.

Figure 10:
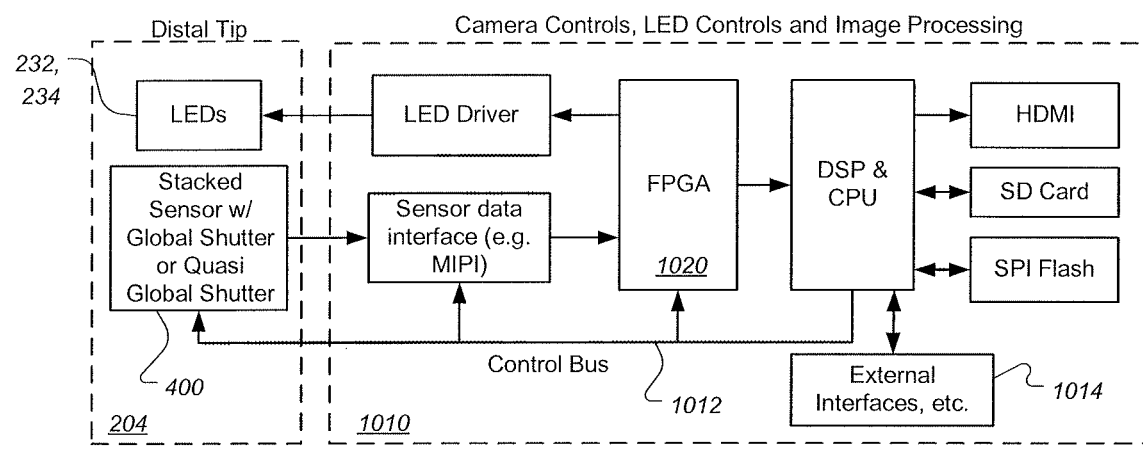
FIG. 10 is a block diagram illustrating aspects of a multi-color band endoscope, according to some embodiments.

FIG. 10 is a block diagram illustrating aspects of a multi-color band endoscope, according to some embodiments. As shown, the LEDs (e.g. 232 and 234 shown in FIG. 2) and BIS CMOS image sensor (CIS) stack 400 (also shown in FIGS. 4B and 7) are located in the distal tip assembly 204. The camera controls, LED controls and image processing 1010 is handled elsewhere in the endoscope, such as in the handle and/or display module. In cases where a portion of the endoscope is configured for single-use and other portions are re-usable, the components 1010 can be located in the re-usable portion(s). Note that a field programmable gate array (FPGA) 1020 can be provided to handle some pre-processing such as de-mosaicing, gain modification, etc. The control bus 1012 can use, for example, IC2 protocol. The external interfaces 1014 can be used, for example, to receive user input such as from buttons and/or touch screen displays. Such input could be used, for example, to make image adjustments, lighting adjustments and/or select either an "all-white" or "all-blue" rather than the default combined white mode and blue mode overlaid image.

Figure 11:
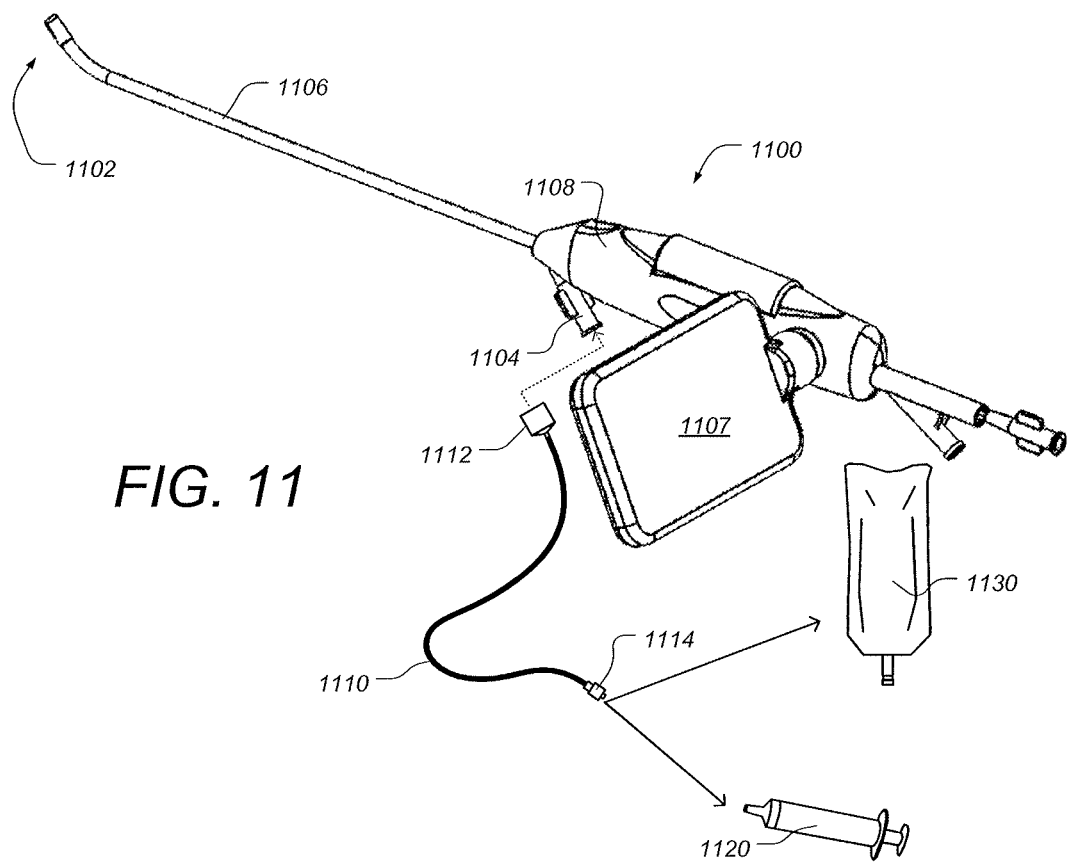
FIGS. 11 and 12 are diagrams of a portable endoscope with disposable cannula, according to some embodiments.
Figure 12:
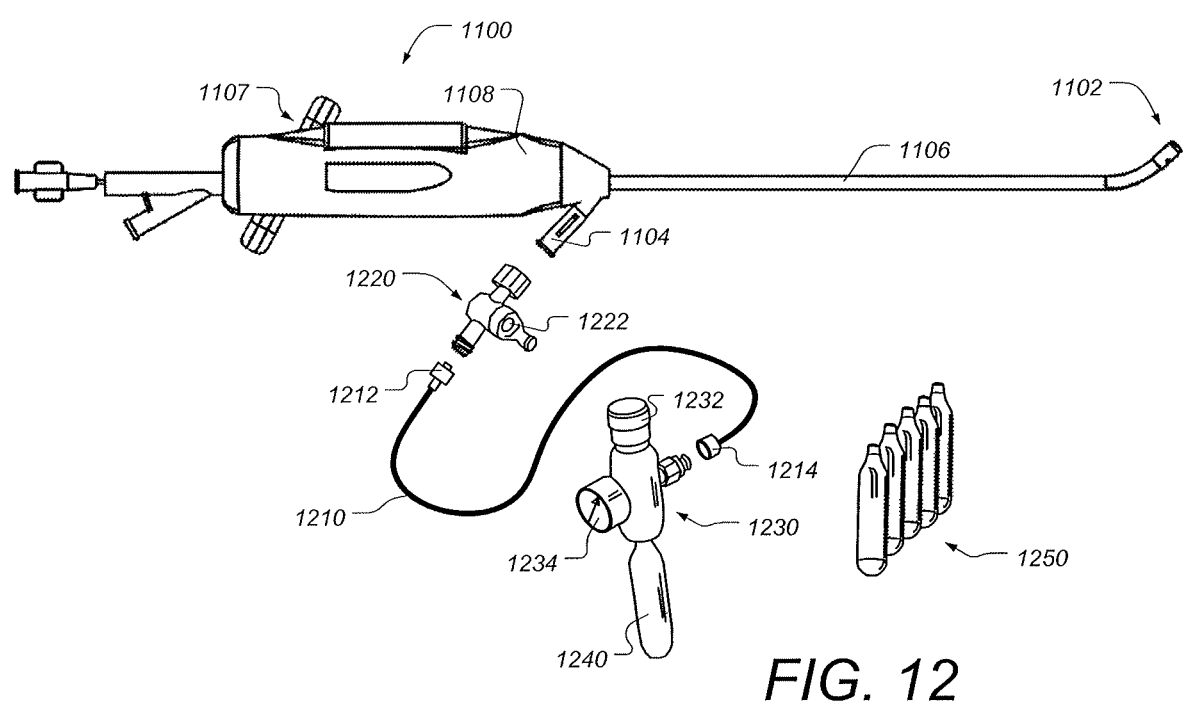

FIGS. 11 and 12 are diagrams of a portable endoscope with disposable cannula. Endoscope 1100 is similar or identical to endoscope 200 in many or all respects. Like endoscope 200, endoscope 1100 can be disposable or partially disposable after a single-use. Endoscope 1100 has a detachable cannula 1106 with at least one fluid channel between distal tip 1102 and fluid port 1104. As in the case of distal tip 204 of endoscope 200, distal tip 1102 of endoscope 1100 includes a camera module and LED light source(s) that are similar or identical as shown described for distal tip 204, supra. Endoscope 1100 also includes a display module 1107 and a handle portion 1108 that can be re-usable. The camera controls, LED controls and image processing 1010 shown in FIG. 10 can be included and located in handle portion 1108 and/or display module 1107.

In FIG. 11, the endoscope 1100 is shown configured for using a liquid (such as saline) to distend or insufflate a target organ such as a bladder. In FIG. 12, the endoscope 1100 is shown configured for using a gas (such as $CO_2$) to distend or insufflate the target organ. In the case of liquids being used for distention/insufflation as shown in FIG. 11, either a hanging fluid bag 1130 or a fluid pump such as a large syringe 1120 can be connected via connector 1114 to tubing 1110. Tubing 1110 can be attached via connector 1112 to luer connector 1104 on endoscope 1100. The fluid can then be infused into the target organ via distal tip 1102 of endoscope 1100.

In FIG. 12, endoscope 1100 is shown configured for using gas, such as $CO_2$ to distend or insufflate the target organ. In this case, a kit is used to connect a gas source, such as a single use cartridge 1240 of $CO_2$ gas to the fluid port 1104 of endoscope 1100. Cartridge 1240 can be a conventional threaded "soda charger" cartridge containing less than 10 grams of carbon dioxide. The kit includes a simple adaptor 1230 that connects the cartridge 1240 on one end and a valve or flow regulator 1232. The adaptor 1230 includes a luer connector connect to endoscope 1100 via tubing 1210. According to some embodiments, adapter 1230 also includes a pressure meter 1234. Tubing 1210 includes luer connectors 1214 and 1212 for attachment to adapter 1230 and flow controller valve 1220. According to some embodiments, flow controller valve 1220 includes valve 1222 that can be configured to prevent back flow of gas from the endoscope towards tubing 1210. Also shown in FIG. 12 are additional gas (e.g. $CO_2$) cartridges 1250. According to some embodiments, the entire kit shown in FIG. 12, including valve 1220, tubing 1210 and adapter 1230 can be relatively inexpensive to manufacture. According to some embodiments the total manufacturing cost of the kit, including gas cartridge 1240 is about 1.0 USD or less. The entire set of a cannula, handle, gas source and gas controller can be a self-contained endoscope that is conveniently hand-held, easily operated by a single person, and easily transported.

It has been found that white light and fluorescence endoscopy with gas insufflation can result in substantial advantages over liquid insufflation. For example, in endoscopy insufflation using gas such as $CO_2$ can result in widening the field of view (FOV) of the lens when compared to fluid medium being used for distention. The increase in FOV can be attributed to a greater index of refraction mismatch between the lens material (e.g. glass or polymer) and gas (e.g. $CO_2$) when compared to liquid (e.g. saline). It has been found in some cases that the FOV can be increased by 15%, 20%, 30% or greater by using gas instead of liquid.

Using gas instead of liquid for insufflation can also keep the patient dry, which can reduce the risk of fluid damage to various devices used in the medical procedure. There can be significant cost savings using $CO_2$ instead of liquid such as saline. Portability can be increased.

In the case of fluorescence imaging, a lack of fluid medium reduces the effect of optical scattering and of secondary undesired light sources such as phosphorescence. In a liquid medium such as water, absorption increases significantly from blue to red, which decreases the signal of desired fluorescence when using those wavelengths. In water, absorption increases to near 0.5 (m−1) around 600 nm. In comparison, $CO_2$ gas is almost transparent to visible light. The decrease in photon absorption/increase in transmission of gas over liquid for the wavelengths of interest (e.g. blue light endoscopy) can lead to significant increases in the signal to noise ratio.

One potential drawback of using gas rather than liquid for insufflation is that the endoscope lens can more easily become tainted with human body fluid such as sticky mucosa or blood. This may cause the resulting image to become blurry. According to some embodiments, when using liquid for distention/insufflation, the liquid flow or the liquid itself and sometimes, in combination of hydrophobic coating of the lens surface, is used to keep the lens relatively clean.

According to some embodiments, when using gas for distension/insufflation the distal tip is configured to direct the flow of the gas to have pattern such that the lens surface can be kept clean. Examples of such designs are shown in FIGS. 13, 14A, 14B and 15.

Figure 13:
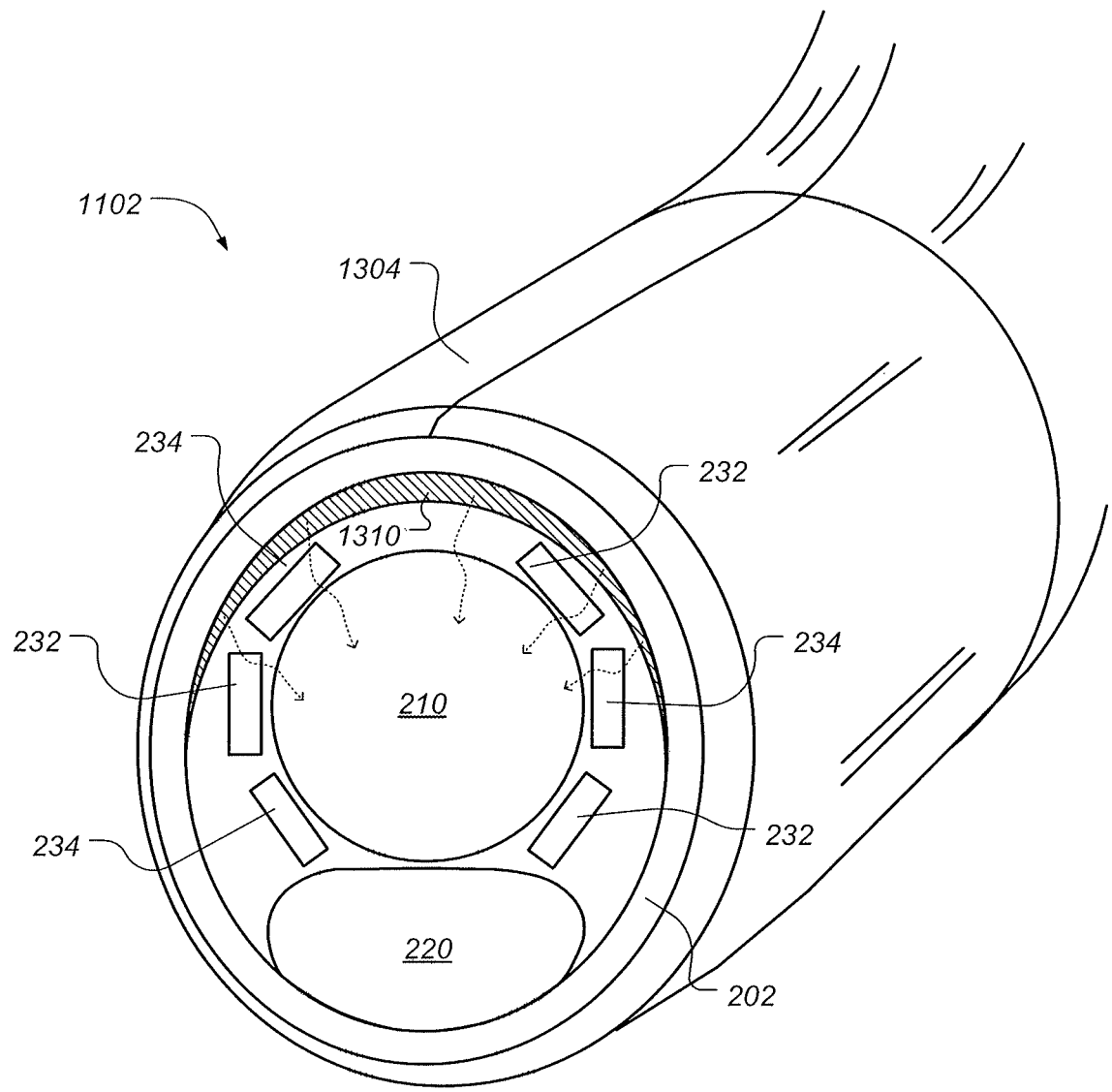
FIG. 13 is a perspective view illustrating aspects of a distal tip of an endoscopic cannula configured for using gas to insufflate a target organ, according to some embodiments.

FIG. 13 is a perspective view illustrating aspects of a distal tip of an endoscopic cannula configured for using gas to insufflate a target organ, according to some embodiments. The distal tip 1102 includes an outer shell 1304 which can be formed from part of the same material as main portion of the elongated cannula (see, e.g. cannula 1106 in FIG. 12). According to some embodiments, the distal tip assembly 1102 can be formed separately and bonded to the end of cannula 1106. Blue LEDs 232, white LEDs 234, lens/sensor barrel 210, and port 220 can be similar or identical to those shown and described supra. The configuration shown in FIG. 13 further includes a gap or spacing 1310 that is in fluid communication with a lumen within cannula 1106 (shown in FIG. 12) which is in turn connected to gas source at the proximal end via a port 1104 (also shown in FIG. 12). According to some embodiments, the gap 1310 is shaped so as to allow gas flow tangentially along the distal surface of lens/sensor barrel 210, as illustrated by the dotted arrows. According to some embodiments, the gas flow can be further directed toward the port 220 (which can be configured to allow passage of a device or tool as described supra). By directing the gas tangentially across the LEDs, camera lens surface working channel port, the gas can be used to prevent collection and/or remove human body fluid or material that might otherwise fully or partially occlude any of those components.

According to some embodiments, since the exit gas flow is directed towards the lens, LEDs and/or port, rather than distally toward the object to be visualized, intermittent higher gas pressure can be used to "blow away" or remove any sticky debris that may adhere to the surfaces of the lens, LEDs and/or port.

Figure 14A:
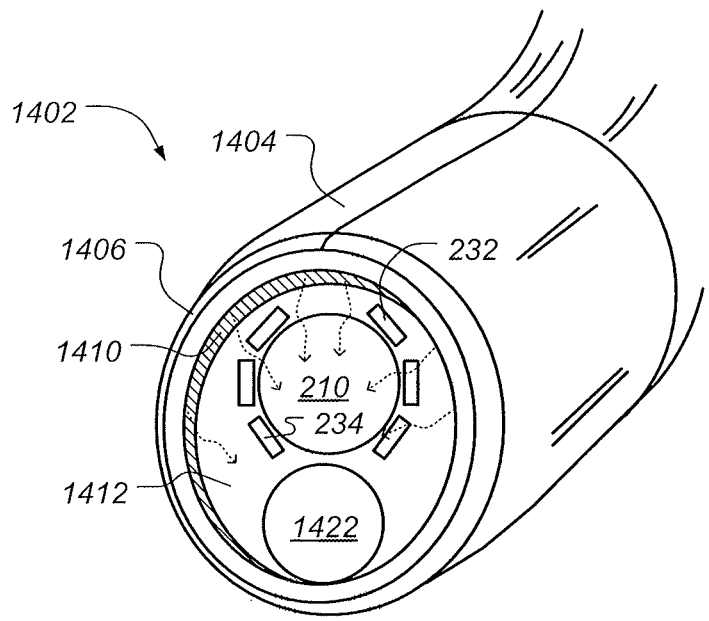
FIGS. 14A and 14B are perspective and cross section diagrams illustrating further aspects of a distal tip of an endoscopic cannula configured for using gas to insufflate a target organ, according to some embodiments.
Figure 14B:
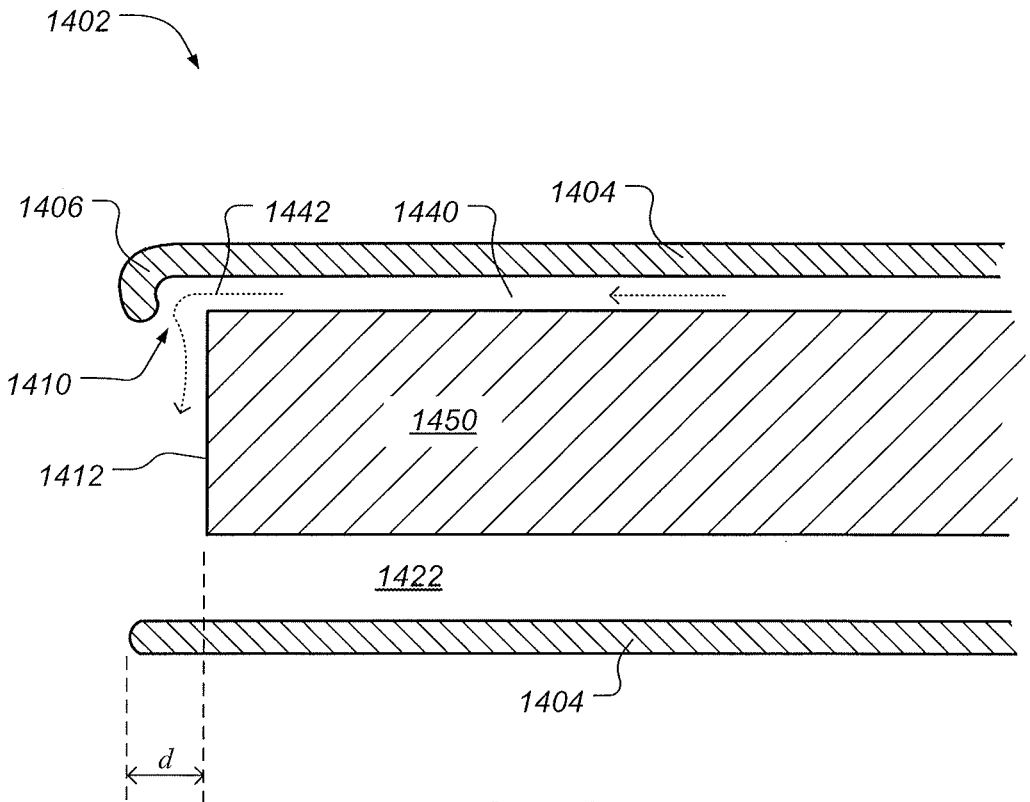

FIGS. 14A and 14B are perspective and cross section diagrams illustrating further aspects of a distal tip of an endoscopic cannula configured for using gas to insufflate a target organ, according to some embodiments. Distal tip 1402 can be similar to tip assemblies 1102, and 204 shown and described supra. Blue LEDs 232, white LEDs 234 and lens/sensor barrel 210 can be similar or identical to those shown and described supra. The distal tip 1402 includes an outer shell 1404 which can be formed from part of the same material as main portion of the elongated cannula (see, e.g. cannula 1106 in FIG. 12). According to some embodiments, the distal tip assembly 1102 can be formed separately and bonded to the end of cannula 1106. A working channel 1422 can optionally be provided in the cannula and have a port formed on distal face 1412 similar to port 220 shown and described supra. As shown in FIG. 14B, the front face 1412 of the distal tip is recessed slightly from the outer rim 1406 by a distance d. It has been found that a curved shape of the rim or lip 1406 and the slight recession of the front face 1412 can be effective in creating a gas flow pattern that is effective in removing or preventing collection of any debris on the lens and/or LED surfaces. According to some embodiments, as in the case of the embodiment shown in FIG. 13, a higher gas pressure can be used to intermittently "blow away" or help remove sticky debris that may adhere to the surfaces of the lens, LEDs and/or port. Note that when designing the recessed distance "d" and the shape and size of the rim 1406, care should be taken not to overly restrict the field of view of the camera module.

Figure 15:
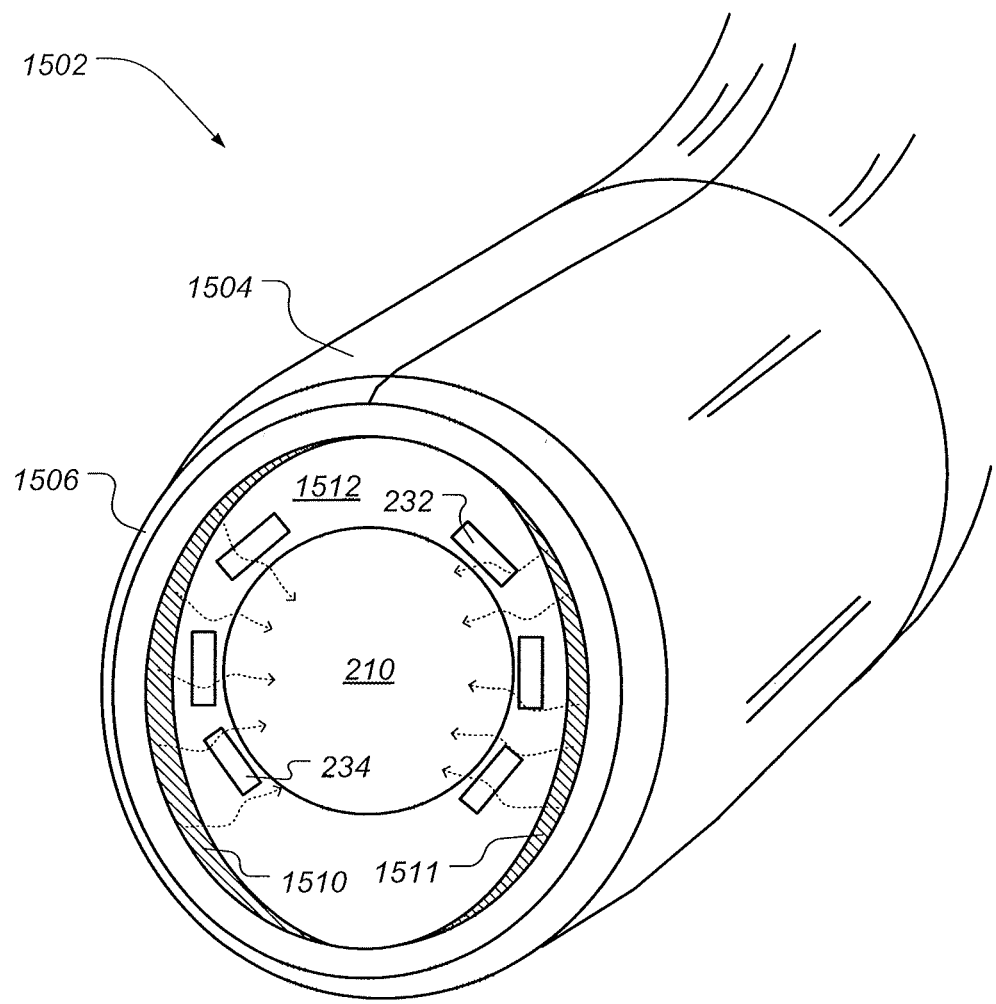
FIG. 15 is a perspective view illustrating further aspects of a distal tip of an endoscopic cannula configured for using gas to insufflate a target organ, according to some embodiments.
Figure 16:
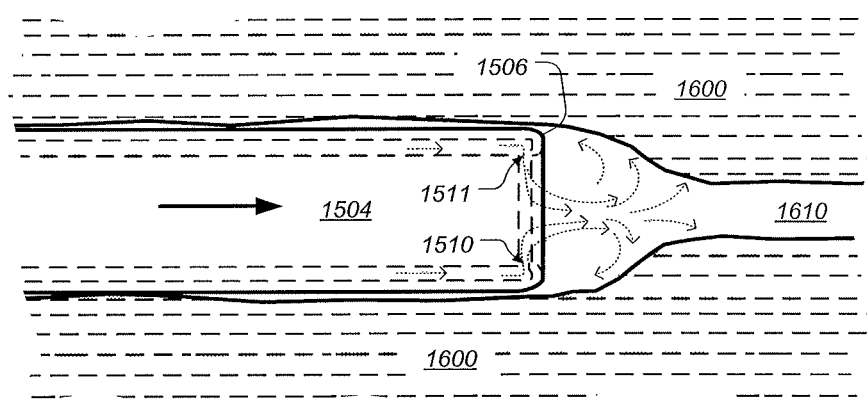
FIG. 16 a diagram showing a handheld surgical endoscope configured for using gas to insufflate a target organ being inserted in a tissue passageway, according to some embodiments.

FIG. 15 is a perspective view illustrating further aspects of a distal tip of an endoscopic cannula configured for using gas to insufflate a target organ, according to some embodiments. Distal tip 1502 can be similar to tip assemblies 1402, 1102, and 204 shown and described supra. Blue LEDs 232, white LEDs 234 and lens/sensor barrel 210 can be similar or identical to those shown and described supra. A separate device channel port and/or fluid port is not shown but can be included. The distal tip 1502 includes an outer shell 1504 which can be formed from part of the same material as the main portion of the elongated cannula (see, e.g. cannula 1106 in FIG. 12). In this example, two crescent-shaped gaps 1510 and 1511 are configured to create opposing gas flow as shown by the dotted arrows. The airflow pattern can be effective to prevent collection and remove any sticky debris that may adhere to the surfaces of the lens and/or LEDs. The front face 1512 can be recessed and/or the rim or lip 1506 can be shaped to generate gas flow that is tangential to the surface of face 1512 as shown and described with respect to FIGS. 14A and 14B. In addition, the opposing gas flows from gaps 1510 and 1511 be configured to form a pattern above the lens surface which extends distally from the cannula can aid insertion of the distal tip and cannula through a tissue passageway and/or into the target organ, as is illustrated in FIG. 16. According to some embodiments, other numbers of gaps and/or different air flow patterns can be used to create gas flow patterns that are also useful in reducing obstruction of the lens and LEDs and/or aid in insertion of the endoscope.

FIG. 16 a diagram showing a handheld surgical endoscope configured for using gas to insufflate a target organ being inserted in a tissue passageway, according to some embodiments. The distal tip 1504 and cannula of a surgical endoscope such as shown and described supra is shown being inserted in passageway 1610 within tissue 1600. As shown, the passageway 1610 is being dilated by the distal tip 1510. In this illustration, the insertion of tip 1504 is being enhanced due to gas envelope or "dome" being formed in front of (or distally) from tip 1504, as depicted by the dotted arrows. The gas ports on opposite sides of tip 1504 as shown in FIG. 15, are configured to form a pattern distally of the lens surface such that a gas envelope or "dome" is formed which shield the lens surface as well as dilate the passageway 1610.

Although the foregoing has been described in some detail for purposes of clarity, it will be apparent that certain changes and modifications may be made without departing from the principles thereof. It should be noted that there are many alternative ways of implementing both the processes and apparatuses described herein. Accordingly, the present embodiments are to be considered as illustrative and not restrictive, and the body of work described herein is not to be limited to the details given herein, which may be modified within the scope and equivalents of the appended claims.

What it claimed is:

1. A single-use, disposable cannula for multi-band imaging of a patient's internal organ, said cannula comprising:
   an imaging structure at a distal portion of the cannula;
   a gas inlet port that is at a proximal portion of the cannula and is configured to receive insufflating gas, a gas outlet port at the distal portion of the cannula, and a gas conduit between said gas inlet port and gas outlet port, wherein said gas outlet port is configured to direct insufflating gas delivered thereto through said gas conduit in a flow over said imaging structure configured to clear the imaging structure;
   a source of insufflating gas under pressure selectively coupled to said gas inlet port to supply insufflating gas thereto;
   wherein said imaging structure at the distal portion of the cannula further comprises:
   a light source configured to illuminate said internal organ with white light from a white LED and with non-white light from a narrow-band, non-white LED, wherein the white LED and the non-white LED illuminate the internal organ from different angles;
   a multi-pixel, backside-illuminated, two-dimensional white light sensor array configured to image white light from the organ and to generate white light image data;
   a multi-pixel, backside-illuminated, two-dimensional non-white sensor array configured to image non-white light from the organ and to generate non-white light image data; and
   a readout circuit electrically and physically integrated with said white light sensor array and said non-white light sensor array into a circuit stack; and
   wherein the white light image data and the non-white light image data represent respective white and non-white images of the organ that are both spatially and temporally registered with each other.

2. The cannula of claim 1, in which the white light sensor array and the non-white light sensor array comprise a single plane of pixels with RGB filters and a readout shutter configured to selectively read out all pixels to thereby produce said white light image data or only pixels responding primarily to non-white light to thereby produce said non-white light image data.

3. The cannula of claim 1, in which the non-white light is present over the entire range of 350-450 nanometers.

4. The cannula of claim 1, in which the non-white sensor array is configured to image light in the 600 or 610 nm wavelength range.

5. The cannula of claim 1, in combination with a handle to which the proximal portion of the cannula is releasably secured through electrical and mechanical couplers tool-free by hand and detached tool-free by hand, said handle further comprising a physically integral video screen that is laterally offset from the cannula and is coupled with said imaging structure to receive and display said white light and non-white light images overlaid in spatial registration such that the non-white image highlights tissue of interest in a normal white image.

6. The cannula of claim 1, in which said white light sensor array and said non-white light sensor array are side-by-side in the same plane.

7. The cannula of claim 1, in which said white light and non-white light illuminate respective fields of illumination in the organ that at least partly overlap.

8. The cannula of claim 1, further including a sterile packaging enclosing the cannula, wherein the cannula is a single-use, disposable unit.

9. The cannula of claim 1, in which said gas outlet port is configured to direct gas delivered thereto through said conduit in a flow over said imaging structure that clears a field of view of the imaging portion.

10. The cannula of claim 1, further including a handle to which the proximal portion of the cannula is releasably secured through electrical and mechanical couplers tool-free by hand and detached tool-free by hand, said handle further comprising a physically integral video screen coupled with said imaging structure to receive and display said white light and non-white light images, and further including a working channel for surgical tools that extends in a straight line from a proximal end of the handle to a distal portion of the cannula.

* * * * *